(12) United States Patent
Weyler et al.

(10) Patent No.: US 6,190,892 B1
(45) Date of Patent: *Feb. 20, 2001

(54) MICROBIAL PRODUCTION OF INDIGO

(75) Inventors: Walter Weyler, San Francisco, CA (US); Timothy C. Dodge; John J. Lauff, both of Rochester, NY (US); Dan J. Wendt, San Mateo, CA (US)

(73) Assignee: Genencor International, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/560,729

(22) Filed: Nov. 20, 1995

(51) Int. Cl.$^7$ .......................... C07H 21/04; C12N 15/11; C12N 15/70; C12N 15/00

(52) U.S. Cl. .................. 435/170; 435/69.1; 435/195; 435/252.33; 435/252.3; 435/320.1; 435/440; 435/41; 435/455; 536/23.1; 536/23.2; 536/23.7

(58) Field of Search .............................. 435/195, 320.1, 435/252.33, 252.3, 69.1, 440, 41, 170, 455, 471; 536/23.2, 23.7, 23.1

(56) References Cited

FOREIGN PATENT DOCUMENTS

| 0 103887 | 3/1984 | (EP) . |
| 0 366 719 | 10/1989 | (EP) . |

OTHER PUBLICATIONS

Claus, Guenter et al, "Degradation of indole by Alcaligenes spec" XPOO2029896, *Syst. Apppl. Microbiol.*, (1983), 4(2), 169–80 CODEN:SAMIDF99:84881t.

Reidies, A. H. et al: "How oxidation of indigo contributes to the yellowing of acid washed denim" XP002029895, *Chemical Abstracts*, vol. 117, No. 16, 19 Oct. 1992, Columbus, Ohio, US 117:152671.

Franklin et al., "Molecular and functional analysis of the TOL plasmid pWWO from Pseudomonas putida and cloning of genes for the entire regulated aromatic ring meta cleavage pathway", *Proc. Natl. Acad. Sci. USA*, vol. 78, No. 12, Dec. 1981 pp. 7458–7462.

Winter, et al, "Efficient degradation of trichloroethylene by a recombinant escherichia coli," *Biotechnology*, vol. 7, Mar. 1989, pp. 282–285.

*Primary Examiner*—George C. Elliot
*Assistant Examiner*—Sean McGarry
(74) *Attorney, Agent, or Firm*—Susan K. Faris; Genencor International, Inc.

(57) ABSTRACT

There is provided an improved process for the biosynthetic production of indigo, the improvement comprising removing unwanted by-products such as isatin or indirubin from the broth in which such indigo is produced. Isatin can be removed by enzymatic activity using an isatin-removing enzyme such as an isatin hydrolase, or by other techniques such as process parameters (elevated temperature, pH), or by contacting the broth containing the isatin with appropriate adsorption compounds/compositions such as carbon or appropriate resins. Since isatin is the precursor of indirubin, the indirubin levels are decreased as a result of isatin removal.

20 Claims, 13 Drawing Sheets

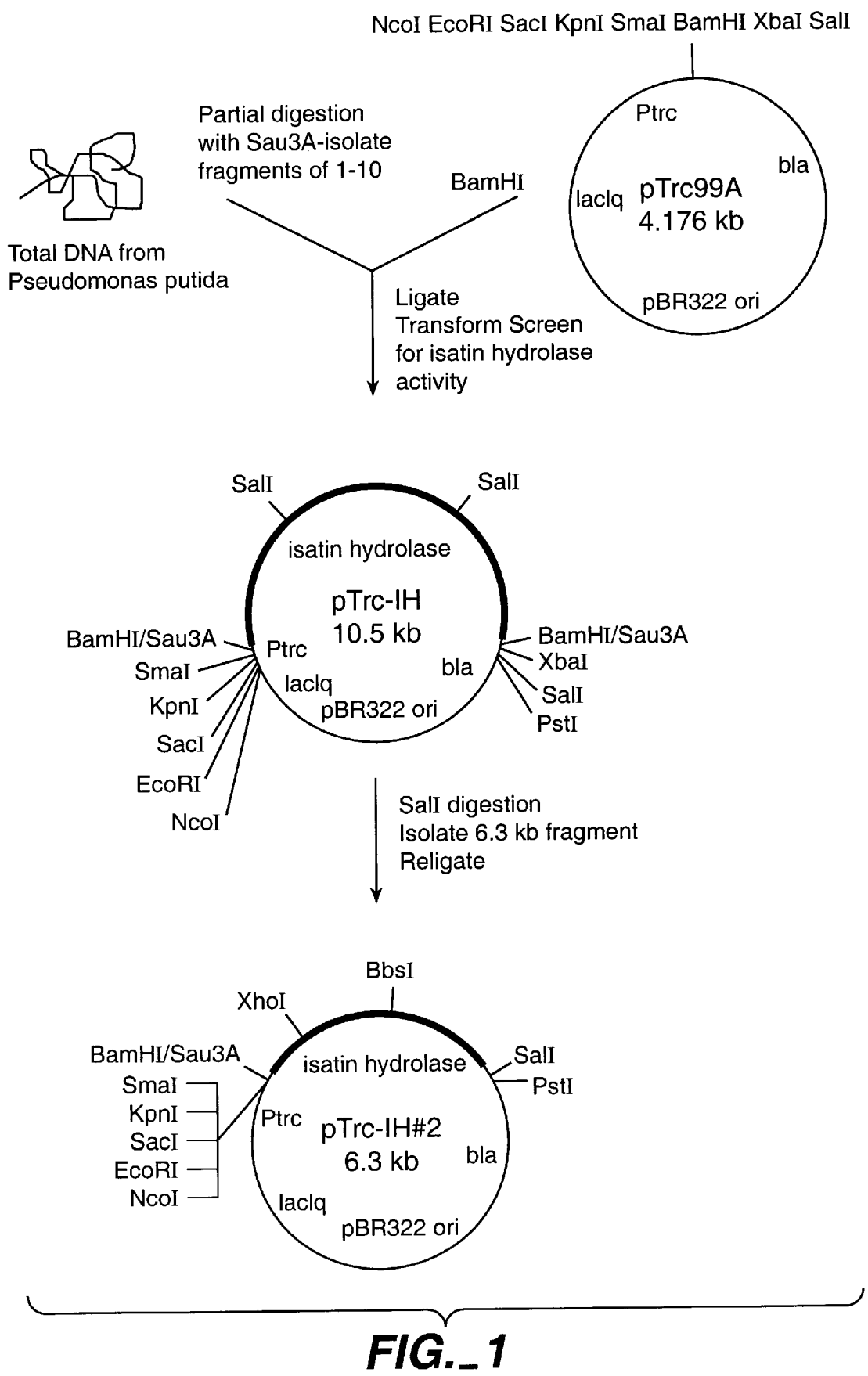
FIG._1

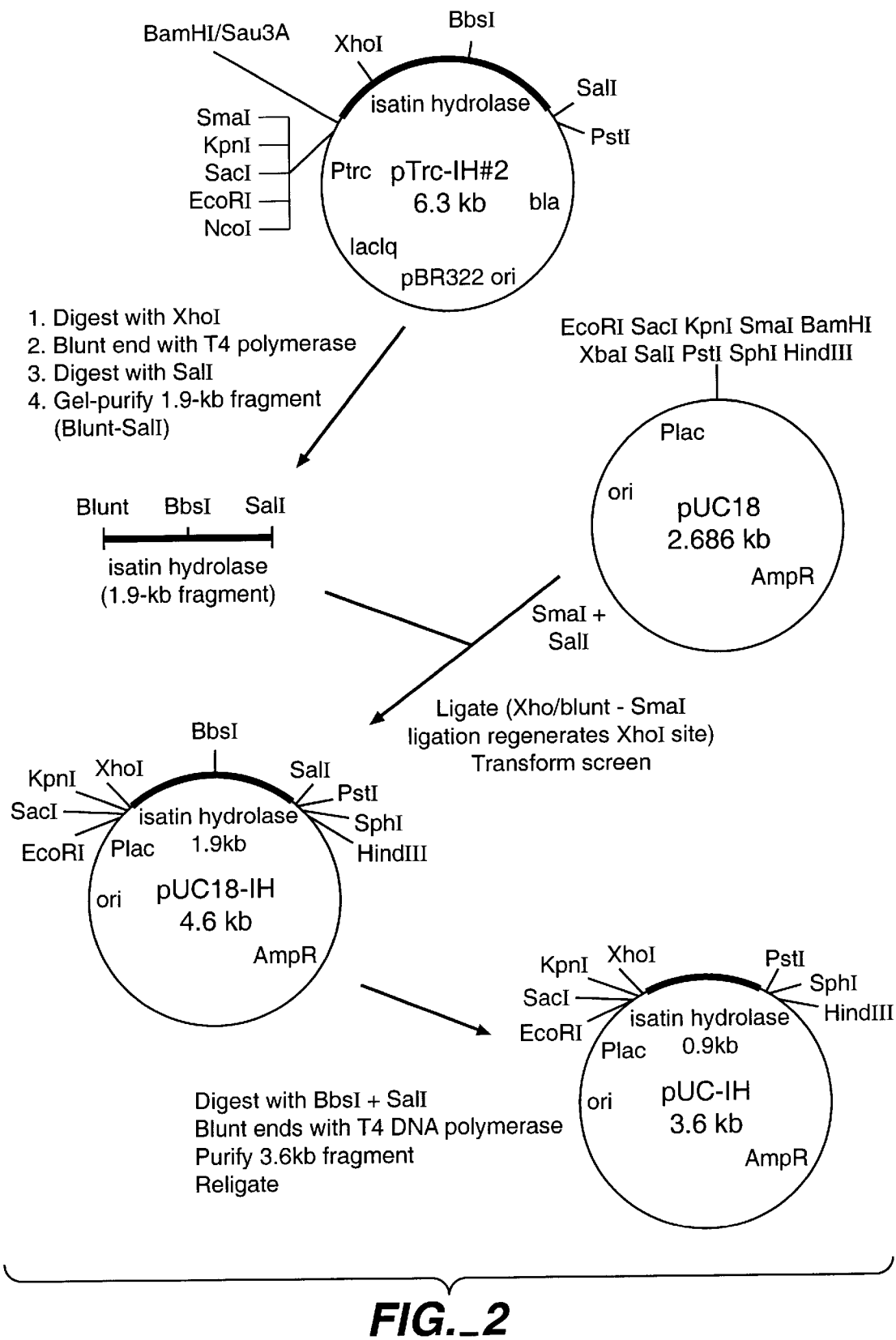
FIG._2

```
GGCGGCGANCCTTCTTAGATTAAAAAGTCGTTTTGCCCCACCCTTTNTGCCCCGGCAGTAATTGTYCAKTATGACATGA
           +         +         +         +         +         +         +         + 80
CCGCCGCTNGGAAGAATCTAATTTTTCAGCAAAACGGGGTGGGAAANACGGGGCCGTCATTAACARGTMATACTGTACT
```

```
                                        Ecl136 II
                                        EcoICRI
                                        Sac I
                                        Sst I
                                           Acc65 I
                                           Acc65 I
                                           Asp 718
                                              Kpn I
TTACGAATTCGAGCTCGGTACCCTCGACTAGCATGATTACGAATTCGAGCTCTTAAGCTTAAGTGCTTAAGCTCTACTAATGCTTAAGCTCTGACCCTCGACCCTCTCTGTCTCT
           +         +         +         +         +         +         +         + 160
AATGCTTAAGCTCGAGCCATGGGAGCTGATCGTACTAATGCTTACGAATTCGAGCTCGAGCTTCGAATTCACGAATTCGAGACTGGGAGCAGAGA
      EcoR I                                             EcoR I
```

```
                                                                    Xho I
                                                                       Sci I

Bpm I
         Gsu I
GCTATAAGATTTATGCAATTTACCCGTCAAGAAAAAACATGAACCCAGCACTTCGGGTTTTTCTGGACTATATGTACCTT
           +         +         +         +         +         +         +         + 240
CGATATTCTAAATACGTTAAATGGGCAGTTCTTTTTTGTACTTGGGTCGTGAAGCCCAAAAAGACCTGATATACATGGAA
```

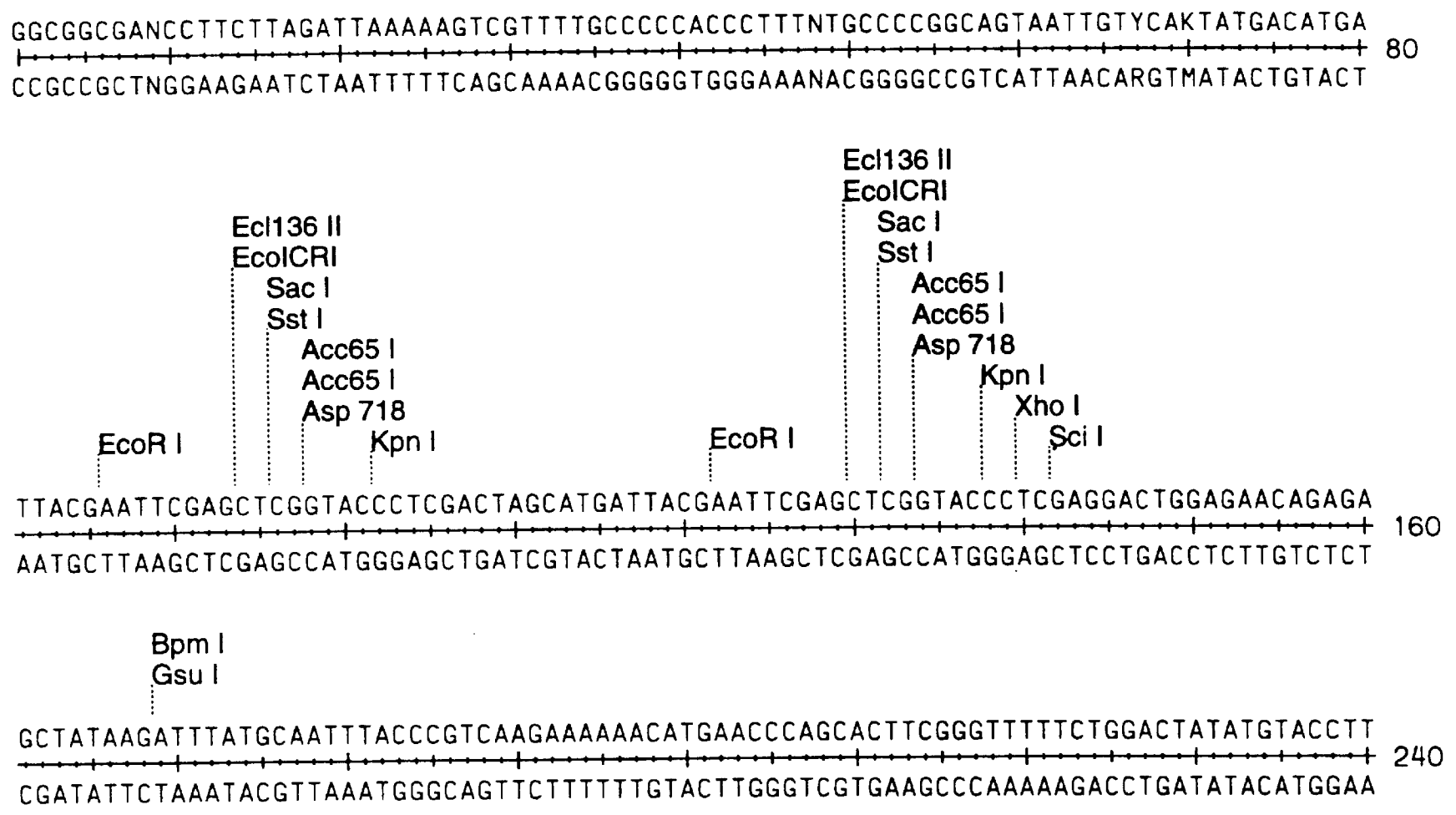

```
                                                                              BstX I
                                                                              .....
GCGGCGAACACACTGGTACTCACTTTGATGCCCCAGTCCATTGGGTCACAGGGCGAATCCGTGCCTGAGAACTCAGTAGAT  560
      |         |         |         |         |         |         |         |
CGCCGCTTGTGTGACCATGAGTGAAACTACGGGGTCAGGTAACCCAGTGTCCGCTTAGGCACGGACTCTTGAGTCATCTA

Cys Gly Glu His Thr Gly Thr His Phe Asp Ala Pro Val His Trp Val Thr Gly Glu Ser Val Pro Glu Asn Ser Val Asp

Acc III
                                                                              BspM II
                    Eco47 III    RleA I                                       Kpn2 I
                    .........    ......                                       ......
CGTATTGACCCACAGCGCTTTATGGCACCGGCAGTAGTGATTGATGCCTCTAAAGAGGTACTAGAAAATCCGGACTGGGT  640
      |         |         |         |         |         |         |         |
GCATAACTGGGTGTCGCGAAATACCGTGGCCGTCATCACTAACTACGGAGATTTCTCCATGATCTTTTAGGCCTGACCCA

Arg Ile Asp Pro Gln Arg Phe Met Ala Pro Ala Val Val Ile Asp Ala Ser Lys Glu Val Leu Glu Asn Pro Asp Trp Val

Acc III
                                                                              BspM II
     Xba I                                                                    Kpn2 I
     .....                                                                    ......
TCTAGAGCCAGAATTTATCCAGGAGTGGGAGAAACTGCATGGCCGGATCGAAGCCGGTTCCTGGTTTCTACTCCGGACAG  720
      |         |         |         |         |         |         |         |
AGATCTCGGTCTTAAATAGGTCCTCACCCTCTTTGACGTACCGGCCTAGCTTCGGCCAAGGACCAAAGATGAGGCCTGTC

Leu Glu Pro Glu Phe Ile Gln Glu Trp Glu Lys Leu His Gly Arg Ile Glu Ala Gly Ser Trp Phe Leu Leu Arg Thr
```

*FIG._3C*

```
                    Bce83 I
                    .....
ATTGGTCGAAGAAAATCAATAACCCGCTTGAGTTTGCTAACCTGATAGACGGGCCACCTCACACGGCCAAGCCCAAGCCAG    800
----+----+----+----+----+----+----+----+----+----+----+----+----+----+----+----
TAACCAGCTTCTTTTAGTTATTGGGCGAACTCAAACGATTGGACTATCTGCCGGTGGAGTGCGGTGCCGGGTTCGGTC

Drd I
.....
                                                                          Bgl I
                                                                          Sfi I
                                                                          .....
Asp Trp Ser Lys Lys Ile Asn Asn Pro Leu Glu Phe Ala Asn Leu Ile Asp Gly Ala Pro His Thr Pro Gly Pro Ser Gln

Esp3 I                    Ssp I
                    .....                     .....
CGTACAGTTGAATGGCTTATCGCCGAACGTGATGTCGTGGGCTTTGAGACGATCAATATTGATGCGGCCTTTC    880
----+----+----+----+----+----+----+----+----+----+----+----+----+----+----+----
GCATGTCAACTTACCGAATAGCGGCTTGCACTACAGCACCCGAAACTCTGCTAGTTATAACTACGCCGGAAAG

Arg Thr Val Glu Trp Leu Ile Ala Glu Arg Asp Val Val Gly Phe Glu Thr Ile Asn Ile Asp Ala Gly Leu Ser

Pst I
                                                            .....
AGGCCCGCTGGGAAGTTCCATACCCTTTGCCACCACAACAAGATGCTGGGAGCAGGACGATTCGGGCTGCAGTGCTTGAACAATC    960
----+----+----+----+----+----+----+----+----+----+----+----+----+----+----+----
TCCGGGCGACCCTTCAAGGTATGGGAAACGGTGGTGTTGTTCTACGACCCTCGTCCTGCTAAGCCCGACGTCACGAACTTGTTAG

Gly Arg Trp Glu Val Pro Tyr Pro Cys His Asn Lys Met Leu Gly Ala Gly Arg Phe Gly Leu Gln Cys Leu Asn Asn
```

FIG._3d

TTGACCTGTTACCACCAACAGGAGCAGTAATCATCTCCGCTCCACTGAAGATCGAAGATGGCTCAGGCAGCCGCTGCGG
AACTGGACAATGGTGGTTGTCCTCGTCATTAGTAGAGGCGAGGTGACTTCTAGCTTCTACCGAGTCCGCTGGGGACGCC

Leu Asp Leu Leu Pro Pro Thr Gly Ala Val Ile Ile Ser Ala Pro Leu Lys Ile Glu Asp Gly Ser Gly Ser Pro Leu Arg
GTACTGGCTATTTTTGATCGAGAATAACTGAGACTACCCTGGGGCCCCAAGTGAGTGTTCTCTA
CATGACCGATAAAAACTAGCTCTTATTGACTCTCTGAGTAGCCGGGTTCACTCACAAGAGAT

Val Leu Ala Ile Phe Asp Arg Glu •

CTCGTAGTAGAAGGCGAAGACCAACTTTCGACCTGCAGGCATGCAAGCTTGGCACTGGCCGTCGTTTTACAACTTTAGCAT
GAGCATCATCTTCCGCTTCTGGTTGAAAGCTGGACGTCCGTACGTTCGAACCGTGACCGGCAGCAAAATGTTGAAATCGTA

FIG._3e

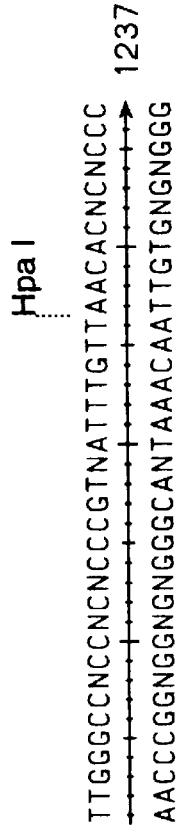
*FIG._3f*
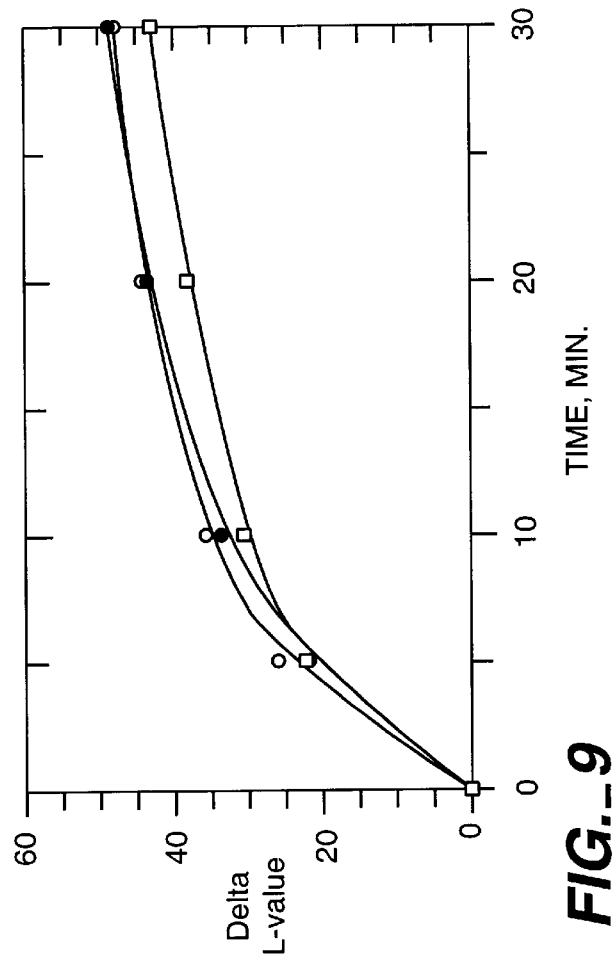
*FIG._9*
*FIG._3*
| Fig._3a |
| Fig._3b |
| Fig._3c |
| Fig._3d |
| Fig._3e |
| Fig._3f |

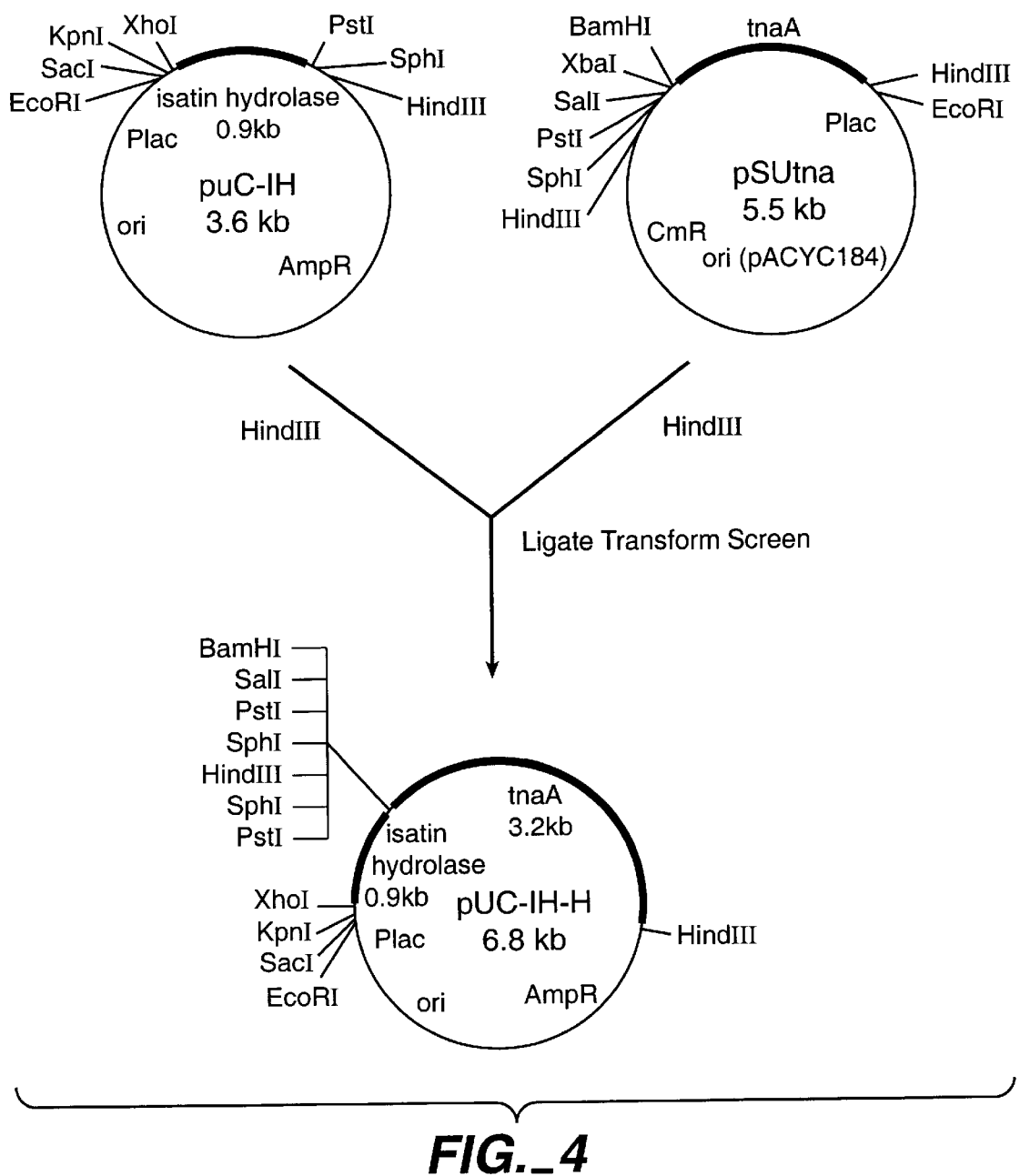
FIG._4

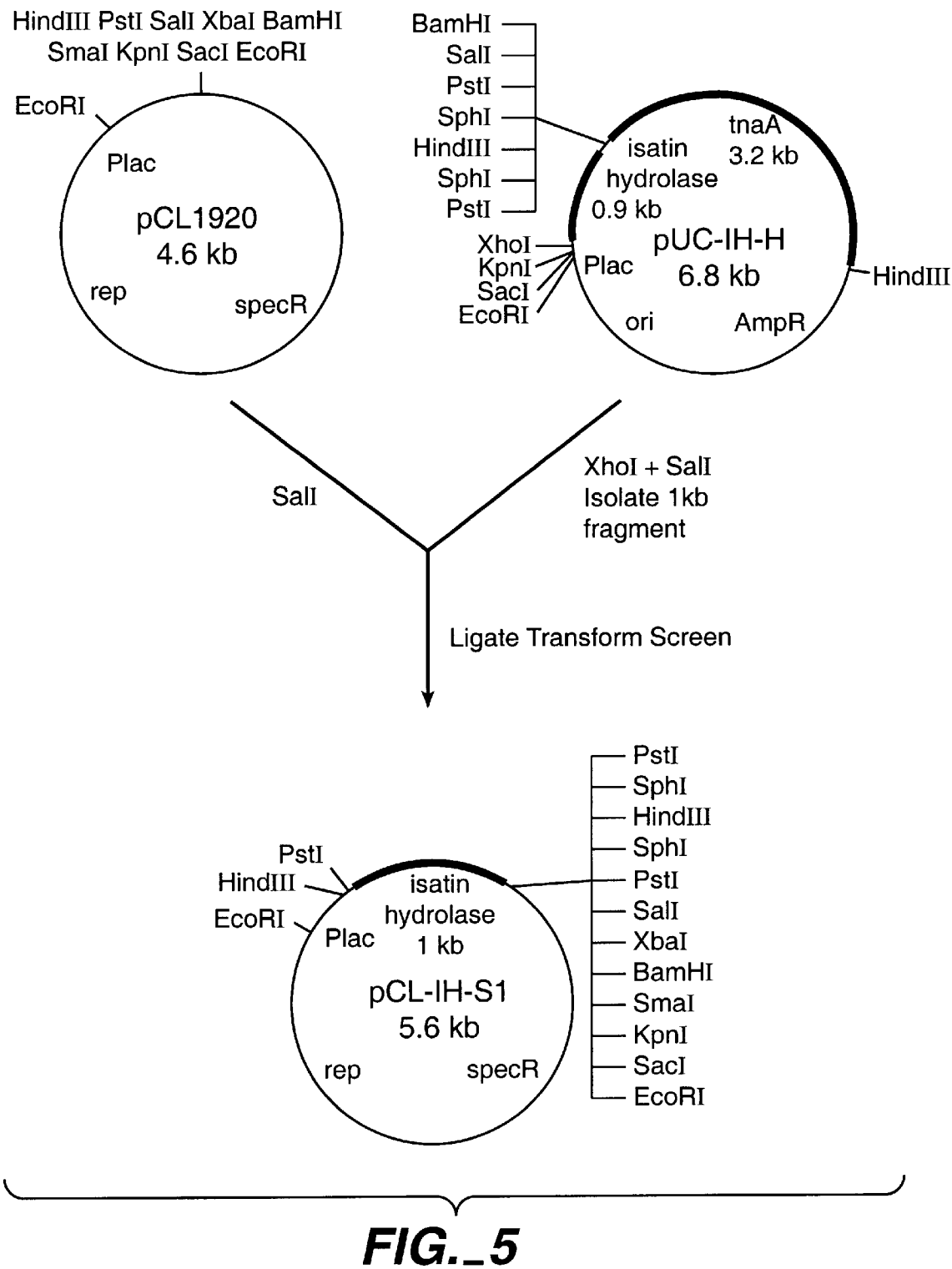
FIG._5

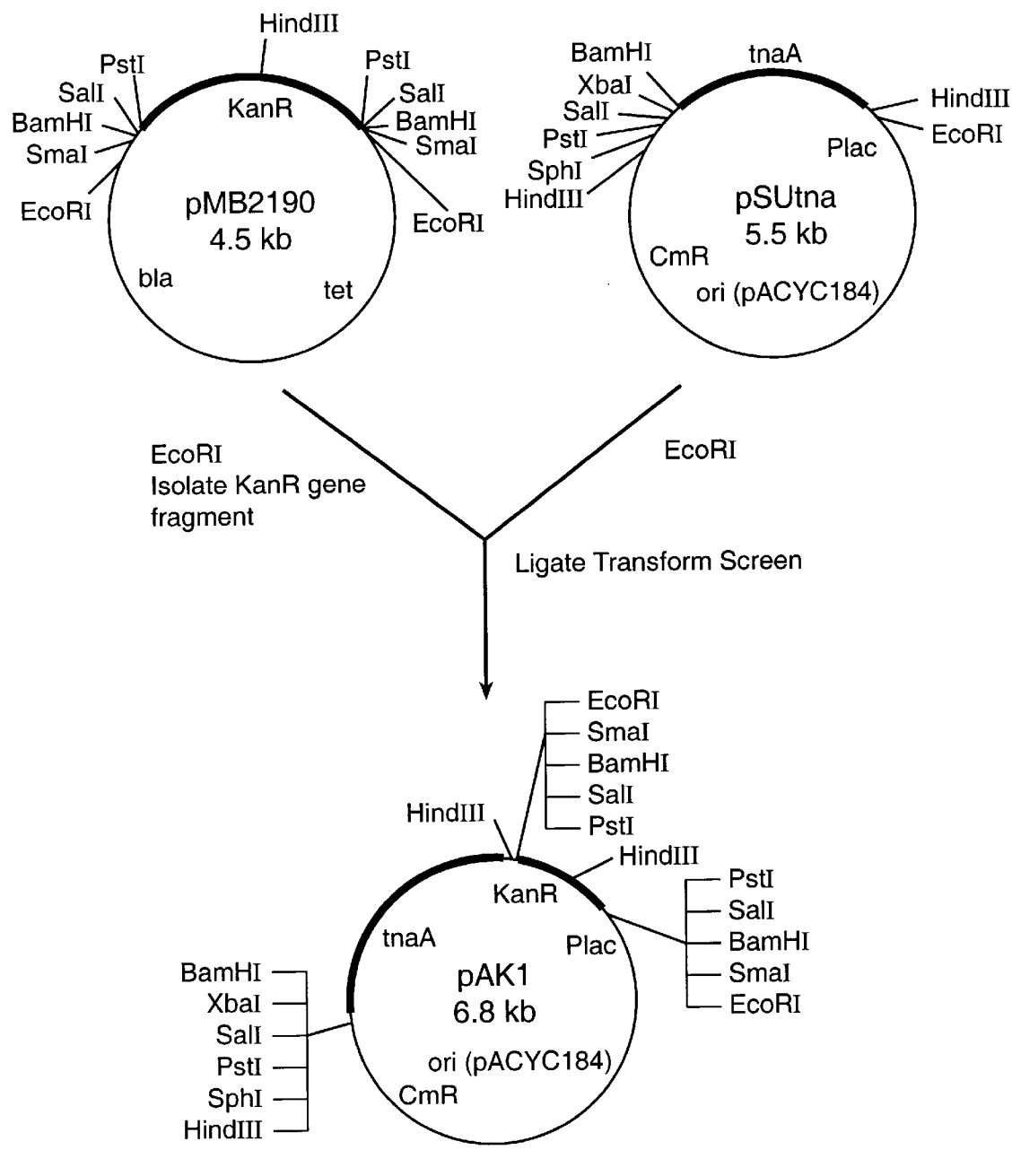
FIG._6

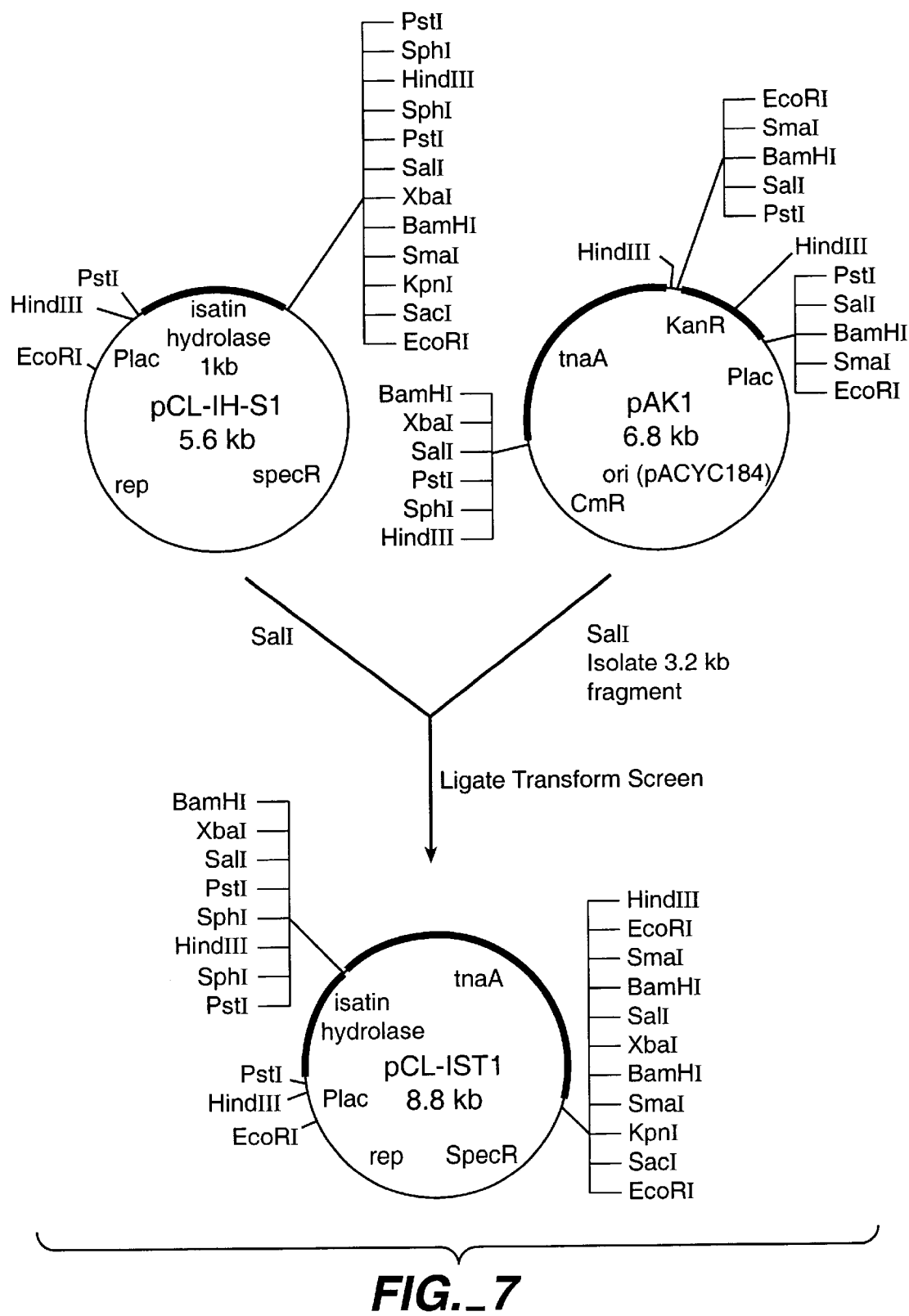
FIG._7

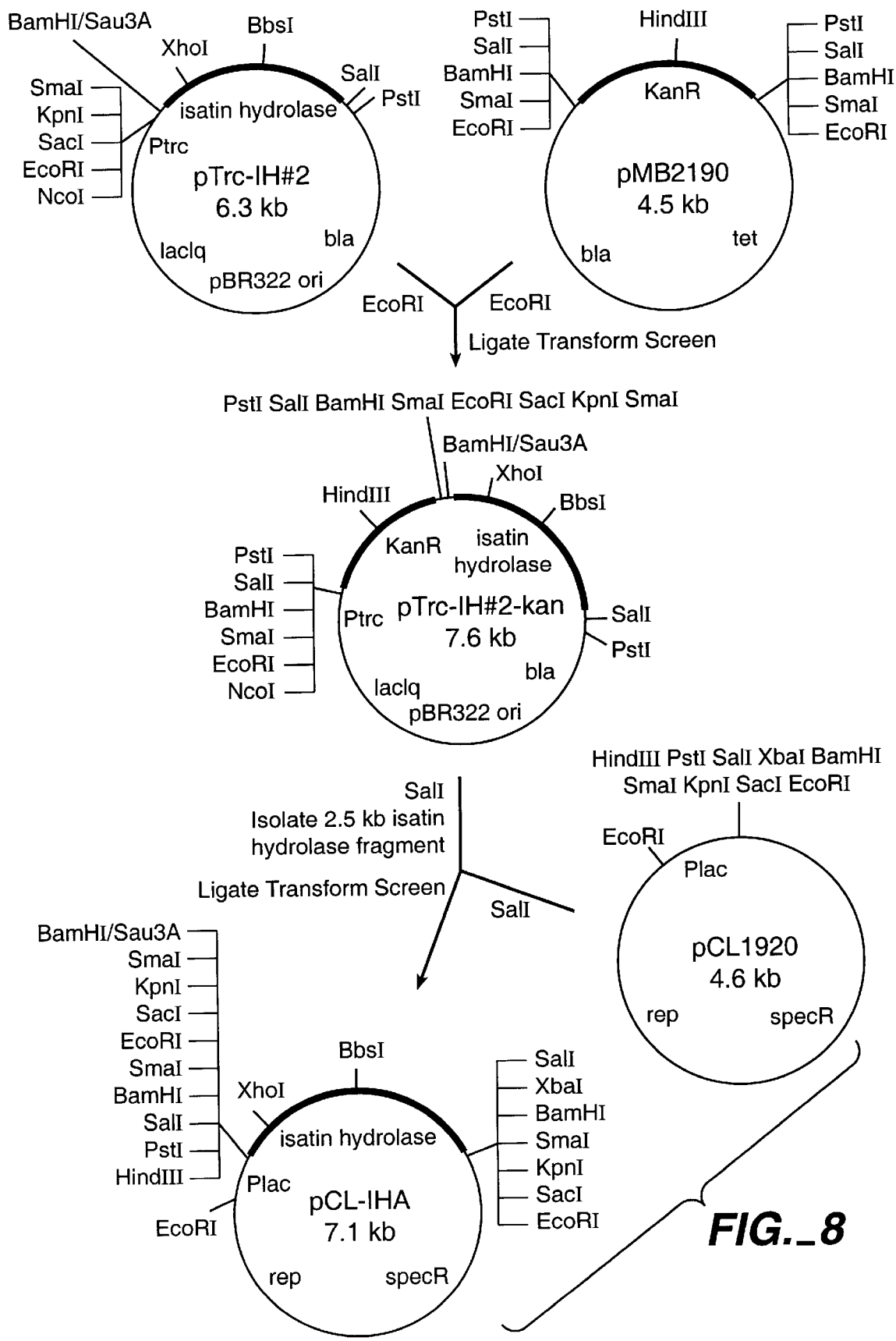
FIG._8

MICROBIAL PRODUCTION OF INDIGO

FIELD OF THE INVENTION

The present invention relates to the biosynthetic production of dye stuff, and particularly indigo, from microorganisms. While the biosynthetic production of indole and tryptophan (both precursors to indigo) have been previously described, the present invention provides an efficient, commercially feasible biosynthetic production system whereby an inhibitory compound in the synthesis of indigo, isatin, is reduced or otherwise removed from fermentation broth. The removal of this inhibitory compound during production of indigo provides enhanced production of the desired end product indigo and/or improved characteristics of the indigo so produced. Furthermore, the present invention prevents or reduces the production of indirubin, a red dyestuff which is a by-product of biosynthetic indigo production.

BACKGROUND OF THE INVENTION

The blue dye indigo is one of the oldest dyestuffs known to man. Its use as a textile dye dates back to at least 2000 BC. Until the late 1800s indigo, or indigotin, was principally obtained from plants of the genus Indigofera, which range widely in Africa, Asia, the East Indies and South America. As the industrial revolution swept through Europe and North America in the 1800s, demand for the dye's brilliant blue color lead to its development as one of the main articles of trade between Europe and the Far East. In 1883 Alfred von Baeyer identified the formula of indigo: $C_{16}H_{10}N_2O_2$. In 1887 the first commercial chemical manufacturing process for indigo was developed. This process, still in use today, involves the fusion of sodium phenylglycinate in a mixture of caustic soda and sodamide to produce indoxyl. The process' final product, indoxyl, oxidized spontaneously to indigo by exposure to air.

Current commercial chemical processes for manufacturing indigo result in the generation of significant quantities of toxic waste products. Obviously, a method whereby indigo may be produced without the generation of toxic by-products is desirable. One such method which results in less toxic by-product generation involves indigo biosynthesis by microorganisms.

Ensley et al. [(1983) *Science* 222:167–169] found that a DNA fragment from a transmissible plasmid isolated from the soil bacterium *Pseudomonas putida* enabled *Escherichia coli* stably transformed with a plasmid harboring the fragment to synthesize indigo in the presence of indole or tryptophan. Ensley et al. postulated that indole, added either as a media supplement or produced as a result of enzymatic tryptophan catabolism, was converted to cis-indole-2,3-dihydrodiol and indoxyl by the previously identified multicomponent enzyme naphthalene dioxygenase (NDO) encoded by the *P. putida* DNA fragment. The indoxyl so produced was then oxidized to indigo upon exposure to air. The dioxygenase described by Ensley et al. is a preferred oxygenase useful in the production of indigo as further described herein.

NDO had previously been found to catalyze the oxidation of the aromatic hydrocarbon naphthalene to (+)-cis-(1R,2S)-dihydroxy-1,2-dihydronaphthalene [Ensley et al. (1982) *J. Bacteriol.* 149:948–954]. U.S. Pat. No. 4,520,103, incorporated by reference, describes the microbial production of indigo from indole by an aromatic dioxygenase enzyme such as NDO. The NDO enzyme is comprised of multiple components: a reductase polypeptide (Rd, molecular weight of approximately 37,000 daltons (37 kD)); an iron-sulfur ferredoxin polypeptide (Fd, molecular weight of approximately 13 kD); and a terminal oxygenase iron-sulfur protein (ISP). ISP itself is comprised of four subunits having an $\alpha_2\beta_2$ subunit structure (approximate subunit molecular weights: $\alpha$, 55 kD; $\beta$, 21 kD). ISP is known to bind naphthalene, and in the presence of NADH, Rd, Fd and oxygen, to oxidize it to cis-naphthalene-dihydrodiol. Fd is believed to be the rate-limiting polypeptide in this naphthalene oxidation catalysis, (see U.S. Pat. No. 5,173,425, incorporated herein by reference, for a thorough discussion of the various NDO subunits and ways to improve them for purposes of indigo biosynthesis).

In addition, aromatic dioxygenases other than NDO may also be useful in the biosynthetic production of indigo, for example, a toluene monooxygenase (TMO) such as that from Pseudomonas (*P. mendocina*) capable of degrading toluene was also able to produce indigo when the culture medium was supplemented with indole. For details, see U.S. Pat. No. 5,017,495, incorporated herein by reference. In principle, any enzyme capable of introducing a hydroxyl moiety into the 3-position of indole to give indoxyl is a candidate for use in the biosynthetic production of indigo.

It has also long been known that microorganisms contain biosynthetic pathways for the production of all 20 essential amino acids, including the aromatic amino acid L-tryptophan. The de novo synthesis of aromatic amino acids (phenylalanine, tryptophan and tyrosine) share a common pathway up through the formation of chorismic acid. After chorismic acid synthesis, specific pathways for each of the three aromatic amino acids are employed to complete their synthesis.

Bacterial biosynthesis of tryptophan from chorismic acid (specifically in *E. coli*) is under the control of the tryptophan (trp) operon. The (trp) operon, comprised of regulatory regions and several structural genes, has been extensively studied because of its complex and coordinated regulatory systems. The regulatory and structural organization of the *E. coli* trp operon, along with the catalytic activities encoded by the structural genes of the operon, appear in FIG. 1 of U.S. Pat. No. 5,374,543, incorporated herein by reference. U.S. Pat. No. 5,374,543 describes improvements in the intracellular production of indole, specifically as it relates to the conversion of indole-3'-glycerol-phosphate (InGP), in conjunction with L-serine, to L-tryptophan. The reaction is catalyzed by the multi-subunit enzyme tryptophan synthase. During the reaction, indole is produced as an intermediate. However, the indole is very rapidly combined with L-serine in a stoichiometric fashion to produce L-tryptophan. Thus, no free indole is produced as a result of this InGP plus L-serine conversion to tryptophan.

However, Yanofsky et al. [(1958) *Biochim. Biophys. Acta.* 28:640–641] identified a tryptophan synthase mutant which led to the accumulation of indole. This particular tryptophan synthase mutant, however, was subject to spontaneous reversion to the wild-type phenotype, as the mutation resulted from a single nucleotide base pair change in the gene coding for the β subunit of tryptophan synthase.

U.S. Pat. No. 5,374,543 describes a method for creating stable tryptophan synthase mutants capable of yielding high levels of intracellular indole. When such indole accumulating tryptophan synthase mutants express an aromatic dioxygenase enzyme like NDO, the accumulated indole may be converted to indoxyl, which can then be oxidized to indigo by molecular oxygen. Thus, through the commercial application of recombinant DNA technology, by the overexpression of a modified trp operon capable of continuously producing indole and an oxygenase enzyme capable of simultaneous conversion of indole to indoxyl, indigo can be produced from a renewable raw material such as glucose.

In shake flask studies applicants have determined that during the synthesis of indigo from indole, low levels of other compounds or by-products accumulate in the culture supernatant. One of these by-products, isatin (indole 2,3-dione), has been found to inhibit the oxygenase (i.e., NDO) activity in the production strain and, consequently, reduces overall indigo production; thus, isatin is undesirable. In addition to the by-product isatin, indirubin, a red dye material derived from isatin, may be produced during this biosynthetic indigo production process. The by-product isatin is believed to reduce the productivity of the production strain, while the by-product indirubin is believed to cause undesirable dyeing characteristics to microbially produced indigo which is expressed as a red cast on cloth dyed with indirubin-tainted microbially produced indigo.

Because the production in shake flasks of one or more of these by-products may either reduce the productivity of this production strain and/or cause undesirable characteristics of the indigo produced therefrom, an object of the present invention is to reduce the buildup of isatin or remove such isatin formed as a by-product of biosynthesis of indigo in microbial cells. Removal of isatin will potentially enhance the overall production of indigo in a fermentor and reduce or prevent the accumulation of indirubin. One method to reduce the buildup of isatin or remove such isatin, as detailed herein, relates to the isolation, cloning, sequencing and expression in indigo-producing host strains of a gene encoding an enzyme having isatin-removing activity. Preferably the enzyme is an isatin hydrolase, an enzyme capable of degrading isatin; however, any method to remove or inhibit isatin formation is contemplated by the present invention. Thus, another aspect of the present invention is the enhanced production of biosynthetic indigo by reducing the buildup or removing accumulated isatin through means, including, but not limited to, enzymatic conversion of the isatin by contacting it with an isatin-removing enzyme such as an isatin hydrolase, general base catalyzed chemical conversion of the isatin at appropriate temperature and pH, or through adsorption of the isatin to carbon or a suitable resin. These aspects of the invention are detailed below.

DEFINITION OF TERMS

The following terms will be understood as defined herein unless otherwise stated. Such definitions include without recitation those meanings associated with these terms known to those skilled in the art.

Tryptophan pathway genes useful in securing biosynthetic indole accumulation include a trp operon, isolated from a microorganism as a purified DNA molecule that encodes an enzymatic pathway capable of directing the biosynthesis of L-tryptophan from chorismic acid. (A. J. Pittard (1987) *Biosynthesis of Aromatic Amino Acids in Escherichia coli and Salmonella typhimurium*, F. C. Neidhardt, ed., American Society for Microbiology, publisher, pp. 368–394.) Indole accumulation is enabled by modification of one or more of the pathway's structural elements and/or regulatory regions. This modified trp operon may then be introduced into a suitable host such as a microorganism, plant tissue culture system or other suitable expression system. It should be noted that the term "indole accumulation" does not necessarily indicate that indole actually accumulates intracellularly. Instead, this term can indicate that there is an increased flux of carbon to indole and indole is made available as a substrate for intracellular catalytic reactions such as indoxyl formation and other than the formation of L-tryptophan. In the context of this invention, the "accumulated" indole may be consumed in the conversion of indole to indoxyl by an oxygenase such as the aromatic dioxygenase NDO, or an aromatic monooxygenase such as TMO, or it may actually build up intracellularly and extracellularly, as would be the case when the desired end product is indole or one of its derivatives.

A suitable host microorganism or host cell is an autonomous single-celled organism useful for microbial indole and/or indigo production and includes both eucaryotic and procaryotic microorganisms. Such host microorganism contains all DNA, either endogenous or exogenous, required for the production of indole, indoxyl and/or indigo, either from glucose or as a bioconversion from tryptophan. Useful eucaryotes include organisms like yeast and fungi or plants. Prokaryotes useful in the present invention include, but are not limited to, bacteria such as *E. coli, P. putida* and *Salmonella typhimurium*.

Biosynthetic conversion of indole to indigo is meant to include indoxyl oxidation to indigo mediated by molecular oxygen or air.

A DNA fragment, as used herein, may encode regulatory and/or structural genetic information. A DNA fragment useful in the instant invention shall also include: nucleic acid molecules encoding sequences complementary to those provided; nucleic acid molecules (DNA or RNA) which hybridize under stringent conditions to those molecules that are provided; or those nucleic acid molecules that, but for the degeneracy of the genetic code, would hybridize to the molecules provided or their complementary strands. "Stringent" hybridization conditions are those that minimize formation of double stranded nucleic acid hybrids from non-complementary or mismatched single stranded nucleic acids. In addition, hybridization stringency may be effected by the various components of the hybridization reaction, including salt concentration, the presence or absence of formamide, the nucleotide composition of the nucleic acid molecules, etc. The nucleic acid molecules useful in the present invention may be either naturally or synthetically derived.

An "exogenous" DNA fragment is one that has been introduced into the host microorganism by any process such as transformation, transfection, transduction, conjugation, electroporation, etc. Additionally, it should be noted that it is possible that the host cell into which the "exogenous" DNA fragment has been inserted may itself also naturally harbor molecules encoding the same or similar sequences. For example, when *E. coli* is used in this invention as the host strain, it is recognized that normally the host naturally contains, on its chromosome, a trp operon capable of directing the synthesis of L-tryptophan from chorismic acid under conditions enabling trp operon expression. A molecule such as this is referred to as an "endogenous" DNA molecule.

A stably transformed microorganism is one that has had one or more exogenous DNA fragments introduced such that the introduced molecules are maintained, replicated and segregated in a growing culture. Stable transformation may be due to multiple or single chromosomal integration(s) or by extrachromosomal element(s) such as a plasmid vector (s). A plasmid vector is capable of directing the expression of polypeptides encoded by particular DNA fragments. Expression may be constitutive or regulated by inducible (or repressible) promoters that enable high levels of transcription of functionally associated DNA fragments encoding specific polypeptides such as the structural genes of a trp operon modified as described herein.

An "isatin-removing enzyme," as used herein, is any enzyme which comprises activity resulting in the inhibition, removal, inactivation, degradation, hydrolysis or binding (sequestering) of isatin, whether such enzyme causes the formation of isatic acid or any other derivative of isatin. A preferred isatin-removing enzyme useful in the present invention is an isatin hydrolase such as the hydrolase isolated from *Pseudomonas putida* (WW2) herein.

Regardless of the exact mechanism utilized for expression of enzymes necessary for the microbial production of indole, indoxyl and/or indigo, it is contemplated that such expression will typically be effected or mediated by the transfer of recombinant genetic elements into the host cell. Genetic elements as herein defined include nucleic acids (generally DNA or RNA) having expressible coding sequences for products such as proteins, specifically enzymes, apoproteins or antisense RNA, which express or regulate expression of relevant enzymes (i.e., isatin hydrolase, tryptophan synthase, NDO, etc.). The expressed proteins can function as enzymes, repress or derepress enzyme activity or control expression of enzymes. Recombinant DNA encoding these expressible sequences can be either chromosomal (integrated into the host cell chromosome by, for example, homologous recombination) or extrachromosomal (for example, carried by one or more plasmids, cosmids and other vectors capable of effecting the targeted transformation). It is understood that the recombinant DNA utilized for transforming the host cell in accordance with this invention can include, in addition to structural genes and transcription factors, expression control sequences, including promoters, repressors and enhancers, that act to control expression or derepression of coding sequences for proteins, apoproteins or antisense RNA. For example, such control sequences can be inserted into wild-type host cells to promote overexpression of selected enzymes already encoded in the host cell genome, or alternatively they can be used to control synthesis of extrachromosomally encoded enzymes.

The recombinant DNA can be introduced into the host cell by any means, including, but not limited to, plasmids, cosmids, phages, yeast artificial chromosomes or other vectors that mediate transfer of genetic elements into a host cell. These vectors can include an origin or replication, along with cis-acting control elements that control replication of the vector and the genetic elements carried by the vector. Selectable markers can be present on the vector to aid in the identification of host cells into which genetic elements have been introduced. Exemplary of such selectable markers are genes that confer resistance to particular antibiotics such as tetracycline, ampicillin, chloramphenicol, kanamycin or neomycin.

A means for introducing genetic elements into a host cell utilizes an extrachromosomal multi-copy plasmid vector into which genetic elements in accordance with the present invention have been inserted. Plasmid borne introduction of the genetic element into host cells involves an initial cleaving of a plasmid vector with a restriction enzyme, followed by ligation of the plasmid and genetic elements encoding for the targeted enzyme species in accordance with the invention. Upon recircularization of the ligated recombinant plasmid, infection (e.g., packaging in phage lambda) or other mechanism for plasmid transfer (e.g., electroporation, microinjection, etc.) is utilized to transfer the plasmid into the host cell. Plasmids suitable for insertion of genetic elements into the host cell are well known to the skilled artisan.

SUMMARY OF THE INVENTION

One aspect of the present invention is the isolation of an organism having an enzymatic activity for removing isatin (designated an isatin-removing enzyme), along with the cloning and sequencing of the gene encoding a preferred isatin-removing enzyme, isatin hydrolase.

Another aspect of the present invention is to incorporate DNA molecules encoding isatin-removing enzymatic activity into host strains capable of producing indole, indoxyl and/or indigo. The DNA molecules are preferably stably transformed, transfected or integrated into the chromosome of a procaryotic or eucaryotic host cell. Useful host cells may be bacteria, yeast or fungi, including, for example, Streptomyces, Escherichia, Bacillus, Pseudomonas, Saccharomyces, Aspergillus, etc. The procaryotic host *Escherichia coli* represents one preferred host organism.

A biologically functional plasmid or viral DNA vector, including a DNA molecule of the invention, represents another aspect of the invention. In one embodiment, a eucaryotic or prokaryotic host cell such as *E. coli* is stably transformed or transfected with such a biologically functional vector.

Other aspects of the invention involve methods for the biosynthesis of indigo in a suitable host microorganism, the method comprising introducing into the host a DNA fragment encoding isatin-removing enzyme activity and cultivating the microorganism under conditions facilitating the accumulation of indoxyl such that upon the conversion of indoxyl to indigo, the isatin-removing enzyme activity removes any isatin by-product produced. Suitable host microorganisms include, but are not limited to, host organism(s) expressing (either endogenously or exogenously) the tryptophan operon (or a modified trp operon) and/or oxygenase activity, which host organism is stably transformed and transfected with a DNA molecule encoding isatin hydrolase. Such organisms are cultivated under conditions facilitating the expression of the tryptophan operon (or modified trp operon), indole oxidizing activity (to allow the formation of indoxyl) and the isatin hydrolase.

Specifically claimed is an improved process for the biosynthesis of indigo in a selected host microorganism comprising introducing into the host microorganism a DNA fragment encoding isatin-removing enzyme activity capable of removing any isatin accumulated during the production of indigo, provided that the host microorganism can be further modified by introducing one or more DNA fragments encoding one or more of the following enzymatic activities:

(i) tryptophanase activity (capable of converting tryptophan to indole) or (ii) oxygenase activity capable of converting indole to indoxyl; and cultivating the modified microorganism under conditions facilitating expression of polypeptides encoded by such DNA fragments such that expression of such polypeptides enables indole accumulation, conversion of indole to indoxyl and removal of isatin. Such modified microorganisms will allow the production of indoxyl, which is oxidized to indigo, and the indigo so produced can then be recovered by means known to those skilled in the art.

Still another aspect of the present invention comprises an improved method for making indigo whereby the production of the by-products isatin and/or indirubin are inhibited or removed by any method, including chemical or enzymatic inhibition/inactivation or adsorption with compounds such as carbon.

BRIEF DESCRIPTION OF THE DRAWINGS

FIG. 1 shows the diagrammatic methodology used to clone the isatin hydrolase gene from *P. putida* strain WW2.

FIG. 2 shows the methodology used to subcdone the isatin hydrolase gene from *P. putida* strain WW2.

FIGS. 3a–f shows the nucleotide sequence of the isatin hydrolase gene (Seq ID No. 1) and the deduced amino acid sequence (Seq ID No. 2), along with the 5' and 3' untranslated sequence (Seq. ID No. 1 1–144 bp and 924–1006 bp, respectively) and polylinker sequence of the cloning vector.

FIG. 4 shows the construction of plasmid pUC-IH-H comprising the isatin hydrolase (IH) and tryptophanase (tnaA) genes.

FIG. 5 shows the construction of plasmid pCL-IH-SI comprising the isatin hydrolase gene in the same orientation as the lac promoter.

FIG. 6 shows the construction of plasmid pAK1, an intermediate plasmid.

FIG. 7 shows the construction of plasmid pCL-ISTI comprising the isatin hydrolase gene in the same orientation as the lac promoter and the tryptophanase (tnaA) gene.

FIG. 8 shows the construction of plasmid pCL-IHA comprising the isatin hydrolase gene in the same orientation as the lac promoter.

FIG. 9 shows the effect on bleaching of indigo-dyed denim due to addition of indirubin to dye.

DETAILED DESCRIPTION OF THE INVENTION

Presently available methods of biosynthetic indigo production may employ the bioconversion of indole to indigo utilizing an aromatic mono- or dioxygenase like TMO or NDO, respectively, or other oxygenase enzymes such as an oxidase from Rhodococcus, as described by S. Hart, K. R. Koch and D. R. Woods [(1992) "Identification of indigo-related pigments produced by *Escherichia coli* containing a cloned Rhodococcus gene," *J. Gen. Microbiology* 138:211–216]. These processes necessitate the addition of indole to the culture medium, as no intracellular indole accumulation occurs in such systems. However, indole added to the culture medium may be toxic to microorganisms. *E. coli* growth may be inhibited when indole is present in media. Bang et al. [(1983) *Biotechnology and Bioengineering* 25:999–1011] described the effects of adding exogenous indole to *E. coli* being grown in shake flasks in minimal media. They found that while concentrations of up to 0.025% slowed bacterial growth, the cells acclimated to the presence of indole over time. However, 0.03% indole severely limited growth with no apparent acclimation, and indole concentrations above 0.04% prohibited growth altogether. In addition, Bang et al., supra, found that L-tryptophan synthesis was inhibited when indole was added at concentrations in excess of 0.2 g/L.

To avoid the inherent limitations of indigo synthesis due to the need for media supplementation with indole, systems capable of endogenous indole biosynthesis have been developed. One such system may employ transferring an exogenous DNA molecule encoding a DNA sequence for a trp operon, modified so as to promote indole production and accumulation (hereinafter "modified trp operon"), into a recombinant host microorganism already capable of expressing an oxygenase (i.e., NDO) activity. Such a system would allow for the production of indigo from glucose or other carbon sources. Optimally, such a system would efficiently convert the endogenously produced indole to indoxyl in a manner avoiding intracellular indole accumulation. A detailed description of this system is found in U.S. Pat. No. 5,374,543, incorporated herein. Such a system in combination with the isatin-removing methods of the present invention is a preferred embodiment of the improved process for indigo production described herein.

Generally, as shown in U.S. Pat. No. 5,374,543, certain point mutations in trpB genes, particularly at position 382 in the trpB gene (designated trpB382), resulted in stable mutants of the trpb. Such mutants lead to enhanced indole flux in the host cells and such mutants are preferred for the production of indigo as described herein in combination with isatin-removing activity. Furthermore, expression of these tryptophan synthase mutants in conjunction with an aromatic dioxygenase such as NDO resulted in the intracellular production of indole and its conversion to indoxyl, which spontaneously oxidized to indigo.

The preferred embodiment of the present invention builds on the teachings of this prior work by addressing the problem of needing to eliminate or reduce the production of the undesirable by-products isatin and/or indirubin during microbial indigo production. Detailed below are specifics regarding the enzymatic, chemical or adsorption methods developed to overcome this problem faced by applicants in their attempts to scale up the biosynthetic production of indigo.

I. Enzymatic Approach to Isatin Formation

Cloning of the Isatin Hydrolase Gene from *Pseudomonas putida* Strain WW2

During the synthesis of indigo from indole, low levels of other compounds accumulate in the culture supernatant. One of these by-products, isatin (indole 2,3-dione), has been found to inhibit NDO activity in the production strain with the consequence of reducing overall indigo yield. Furthermore, isatin is a precursor to indirubin, a red dye which may cause a slight reddish cast on materials dyed with microbial indigo. Methods were, therefore, sought to remove or eliminate buildup of isatin. Accordingly, a search for an enzyme capable of degrading isatin was initiated. Numerous soil samples were screened using a nutritional selection scheme, resulting in the identification of an organism exhibiting the ability to degrade isatin. Taxonomic studies consisting of Biolog®, GC-FAME, gelatin hydrolysis and phospholipase C assays suggest the organism to be a *Pseudomonas putida*. The organism was, therefore, designated *Pseudomonas putida* strain WW2. The enzymatic activity was identified as a hydrolytic reaction in which isatin is hydrolyzed to isatic acid. The enzyme was, therefore, designated 'isatin hydrolase.'

To clone the gene encoding isatin hydrolase (see FIGS. 2 and 3), total DNA was prepared from *Pseudomonas putida* strain WW2 and partially digested with Sau3A restriction endonuclease. The partially digested DNA was then electrophoresed in a 0.7% agarose gel for 12 hours at 100 mV. Following staining with ethidium bromide, the DNA was visualized by fluorescence and a gel slice containing DNA fragments ranging from 1 kb to 10 kb was excised. The DNA was eluted from the gel slice by electroelution and further purified by phenol/chloroform treatment, ethanol precipitation and resuspension in TE buffer.

The isolated DNA fragments were then ligated to the expression vector pTrc99A (commercially available from Pharmacia Biotech, Inc.; catalog #27-5007-01) which was previously linearized by digestion with BamHl and dephosphorylated with calf intestinal alkaline phosphatase. Following ligation, 5 μl of the ligation mixture was used to transform competent *E. coli* Sure Cells® (obtained from Stratagene, catalog #200238). Following the outgrowth of the transformation, the mixture was diluted 1:1 with 2YT medium and plated on L-agar plates containing 50 μg/ml carbenicillin and 1 mM IPTG.

Following overnight incubation of the plates at 37° C., several thousand transformants were observed. Colonies were lysed by spraying the surface of the plates with a solution of 10 mg/ml lysozyme and 25 mM EDTA and incubating for 20 minutes at room temperature. Plates were then overlaid with nitrocellulose membranes previously stained for 20 minutes in a solution consisting of 3.5 mg of 5,7-dimethylisatin in 10 ml of 50 mM Tris/HCl pH 7.5. After a one hour incubation period the nitrocellulose membranes were lifted from the plates and inspected for white clearing zones on an orange background. Such clearing zones would indicate the presence of an isatin hydrolytic activity.

This screen yielded a positive transformant which contained a plasmid with a 6.3 kb cloned insert (FIG. 1). This plasmid was designated pTrc-IH. Subcloning of the isatin hydrolase gene was accomplished by deleting segments of the 6.3 kb insert from pTrc-IH. Digestion of pTrc-IH with SalI gave 3 fragments (1.6 kb, 2.6 kb, and 6.3 kb). This indicated that the cloned insert contained a minimum of two internal SalI sites. The cloning vector contains one SalI site in the polylinker region. When the 6.3 kb SalI fragment of pTrc-IH was isolated, re-ligated, and transformed into competent *E. coli* Sure Cells® (Stratagene, catalog #200238) isatin hydrolase activity was again observed. This new plasmid was designated pTrc-IH#2, and contained the IH gene on a cloned fragment of approximately 2.3 kb (FIG. 1).

Restriction mapping of pTrc-IH#2 revealed the presence of a unique XhoI restriction site in the cloned fragment located approximately 400 base pairs from one of its ends. This permitted further subcloning of the isatin hydrolase-containing fragments (see FIG. 2). pTrc-IH#2 was digested with XhoI followed by filling of overhangs with T4 DNA polymerase (creating blunt ends). The resultant linearized plasmid was then digested with SalI. This generated a 1.9 kb blunt-SalI fragment which was purified from an agarose gel and ligated to the vector pUC18 previously digested with SmaI and SalI. Ligation of a filled-in XhoI overhang to a SmaI end recreates a XhoI site. *E. coli* strain JM101 (ATCC 33876) was transformed with this ligation mixture and transformants having isatin hydrolase activity were identified using the screen described above. The plasmid isolated from the positive transformant was confirmed to contain the isatin hydrolase gene on the 1.9 kb XhoI-SalI fragment; this plasmid was designated pUC18-IH (FIG. 2). Further experiments showed that the isatin hydrolase activity in strains containing pUC18-IH was inducible with IPTG, suggesting that the direction of transcription of the isatin hydrolase gene in pUC18-IH was the same as the lac promoter.

The isatin hydrolase gene was further subcloned as follows (see FIG. 2). Partial DNA sequencing and restriction mapping of the 1.9 kb cloned fragment in pUC18-IH revealed the presence of a BbsI restriction site unique to the fragment and near its center. Approximately 1 kb of the cloned DNA could be deleted by digesting pUC18-IH with BbsI and SalI and separating fragments on agarose gel and isolating the large (3.6 kb) fragment. After filling in ends with T4 DNA polymerase, this fragment was recircularized by ligation. The ligation mixture was then used for transforming *E. coli* strain JM101 (ATCC 33876) and screening for isatin hydrolase activity. A positive clone yielded a new plasmid which was designated pUC-IH (FIG. 2) and was found to contain the functional isatin hydrolase gene within a fragment of about 900 base pairs.

DNA Sequence of the Isatin Hydrolase Gene

The entire cloned insert in pUC-IH was sequenced using the commercially available lac and reverse primers designed for use with pUC vectors (ATCC 37253). The complete nucleotide sequence of the insert is shown in FIG. 3 (Seq ID No. 1). A single open reading frame (780 bp from bp 145 to bp 923 in Seq ID No. 1) within the sequenced region was identified using sequence analyzer software from Genetics Computer Group, Inc. The predicted molecular weight (32,886) of isatin hydrolase based on the nucleotide sequence of this open reading frame was in agreement with the estimated size of isatin hydrolase protein (30,000–40,000) as determined by gel permeation chromatography and native polyacrylamide gel electrophoresis. N-terminal amino acid sequencing of the subsequently purified isatin hydrolase yielded a sequence of MTSIKLLAESLLK (Seq ID No. 3). This sequence is in agreement with the predicted N-terminal amino acid sequence derived from the nucleotide sequence of the single open reading frame. These analyses indicate that there are 144 base pairs 5' (untranslated) and 82 base pairs 3' (untranslated) adjacent to the open reading frame.

Construction of an Auxiliary Plasmid Containing the Isatin Hydrolase Gene and the *E. coli* K-12 Tryptophanase Gene for Use in the Indigo Production Strain The concentration of isatin has been found to be reduced in tryptophan to indigo biotransformation fermentations in the presence of isatin hydrolase when supplied to the fermentation either as a cell extract or when the enzyme was expressed from a plasmid. A separate benefit in the rate of indigo production in shake flasks was observed when tryptophanase, the enzyme that converts tryptophan to indole and is derived from *E. coli* K-12, was overexpressed from a plasmid harboring the tnaA gene. Both the isatin hydrolase and the tryptophanase genes were, therefore, combined on a single low copy number plasmid to effect these benefits. The construction of this plasmid is described below.

During the construction of plasmid pUC-IH, the unique SalI restriction site at the 3' end of the isatin hydrolase gene was destroyed. For convenient subcloning of the isatin hydrolase gene from pUC-IH, a SalI site was recreated at the 3' end of the isatin hydrolase gene by digesting pUC-IH with HindIII, and cloning into this site (in the proper orientation) a 3.2 kb HindIII fragment containing the *E. coli* K-12 tryptophanase (tnaA) gene (from pSUtna, see FIG. 4) [Deeley and Yanofsky (1981) "Nucleotide sequence of the structural gene for tryptophanase of *Escherichia coli* K-12," *J. Bacteriol.* 147:787–796]. The latter fragment was chosen only because it has useful polylinker sequence at one end of the cloned tnaA gene. The new plasmid construction was designated pUC-IH-H (FIG. 4). This new intermediate construction allowed the isatin hydrolase gene to be conveniently removed from pUC-IH-H on a XhoI-SalI fragment of approximately 1 kb.

This fragment was cloned in both orientations into the unique SalI site of the low copy number vector pCL1920 [C. G. Lerner and M. Inouye (1990) *Nucleic Acid Research* 18:4631]. The desired plasmid with the isatin hydrolase gene in the same orientation as the lac promoter and a unique SalI site at the 3' end of the isatin hydrolase gene (see FIG. 5) was isolated and designated pCL-IH-S1.

The cloned *E. coli* K-12 tryptophase (tnaA) gene was added to pCL-IH-S1 as follows: a 1.3 kb EcoRI fragment containing the kanamycin resistance gene from pMB2190 [A. Darzins, B. Frantz, R. I. Vannags, A. M. Chakrabarty (1986) *Gene* 42:293–302] was inserted into the unique EcoRI site at one end of the cloned tnaA gene in plasmid pSUtna. Plasmid pSUtna was constructed by subcloning a 3.2 kb EcoRI-BamHI fragment (containing tnaA) from plasmid pMD6 [M. C. Deeley and C. Yanofsky (1981) *J. Bacteriol.* 147:787–796] into plasmid pSU18 [B. Bartolome, Y. Jubete, E. Martinez, F. de la Cruz (1991) *Gene* 102:75–78]. To introduce an additional SalI site adjacent to the tnaA gene, a 1.3 kb EcoRI fragment containing the kanamyacin resistance gene and two flanking multiple cloning sites from pMB2190 [partial plasmid map is shown in FIG. 8; A. Darzins, B. Frantz, R. I. Vanags, A. M. Chakrabarty (1986) *Gene* 42:293–302] was introduced into the unique EcoRI site, 3' to cloned tnaA in plasmid pSUtna. The resultant plasmid was designated pAK1.

The tnaA gene could be excised from pAK1 as a 3.2 kb SalI fragment. This fragment was inserted into the unique SalI site of pCL-IH-S1 (see FIG. 7). Of the two predicted orientations of the insert, the one in which the orientation of transcription was the same as for isatin hydrolase was isolated and designated pCL-IST1 (FIG. 7).

Construction of the Production Organism

To create the production organism, the compatible plasmids 911-ISP [Ensley et al. (1987) "Expression and complementation of naphthalene dioxygenase activity in *Escherichia coli*" in *Microbial Metabolism and the Carbon Cycle*, S. R. Hagdorn, R. S. Hanson and D. A. Kunz, eds., Harwood Academic Publishers, New York, pp. 437–455] and pCL-IST1 (FIG. 7) were introduced into the production host FM5 [Burnette et al. (1988) "Direct expression of Bordella pertussin toxin subunits to high levels in *Escherichia coli,*" *Bio/technology* 6:699–706] by the standard transformation procedure using FM5 cells rendered competent by calcium chloride treatment. Transformants containing both plasmids were identified by their resistance to ampicillin and spectinomycin conferred by plasmids 911-ISP and pCL-IST1, respectively. The presence of these plasmids in the FM5 host was confirmed by isolation of total plasmid DNA and restriction enzyme analyses.

The production host strain, FM5, was previously described [Burnette et al. (1988) "Direct expression of Bordella pertussin toxin subunits to high levels in *Escherichia coli,*" *Bio/technology* 6:699–706] as was the production plasmid, 911-ISP, and the host FM5/911-ISP [Ensley et al. (1987) "Expression and complementation of naphthalene dioxygenase activity in *Escherichia coli*" in *Microbial Metabolism and the Carbon Cycle*, S. R. Hagdorn, R. S. Hanson and D. A. Kunz, eds., Harwood Academic Publishers, New York, pp. 437–455]. The cloned *E. coli* K-12 tna fragment encoding tryptophanase (tnaA) (3.2 kb) has been described [Deeley and Yanofsky (1981) "Nucleotide sequence of the structural gene for tryptophanase of *Escherichia coli* K-12," *J. Bacteriol.* 147:787–796], as has been the vector pCL1920 [C. G. Lerner and M. Inouye (1990) "Low copy number plasmid for regulated low-level expression of cloned genes in *Escherichia coli* with blue/white insert screening capability," *Nucleic Acid Research* 18:4631]. The only new DNA being introduced into the indigo production strain (FM5/911-ISP, pCL-IST1) is the pCL1920 vector with a 1 kb XhoI-SalI fragment containing the isatin hydrolase gene inserted along with a small amount of sequenced polylinker DNA carried over from intermediate plasmid constructions (see FIG. 8) and the tna DNA coding for tryptophanase.

The application of the isatin hydrolase gene to remove isatin produced as a by-product in an indigo fermentation can take on a number of different forms. We envisage the use of the gene product isatin hydrolase in the bioconversion of tryptophan to indigo (bioconversion method) and in the production of indigo from glucose in a single host organism through the intermediate synthesis of tryptophan or indole by this organism (single host or direct method). The residence of the isatin hydrolase gene can take on several forms itself: the gene would be effective when placed on the chromosome of the host, supplied on a extrachromasomal autonomously replicating DNA element, or any other form of DNA introduced into the cell and maintained for the duration of the fermentation. The regulation of gene expression may be constitutive or may be regulated with a suitable promoter.

When chromosomally incorporated, the hydrolase gene would work in concert with oxygenases such as NDO (U.S. Pat. Nos. 4,520,103 and 5,173,425), TMO (U.S. Pat. No 5,017,495) or an oxidase as exemplified by the oxidase from Rhodococcus [S. Hart, K. R. Koch and D. R. Woods (1992) "Identification of indigo-related pigments produced by *Escherichia coli* containing a cloned Rhodococcus gene," *J. Gen. Microbiology* 138:211–216]. Single component monooxygenases capable of providing indoxyl either directly or indirectly are also candidates for application with isatin hydrolase. These oxygenases/oxidases or components of them could be encoded either on the chromosome of the host or be introduced on extrachromosomal elements. The genes for the oxidative enzymes could be expressed constitutively or be regulated with appropriate promoters. The isatin hydrolase gene could reside on the same DNA element as the gene encoding the oxidizing enzyme. Expression of the genes for all activities may be regulated independently or may be regulated in concert.

In the direct method, i.e., the single host method, the isatin hydrolase gene is expected to be coexpressed along with genes of the aromatic amino acid pathway which could be under endogenous regulation or artificially regulated by engineered mutations which remove feed-back inhibition and/or cause the genes to be overexpressed. This includes aromatic amino acid pathway genes amplified by virtue of being encoded on multi-copy number plasmids from which the appropriate genes are expressed from constitutive promoters or from regulated promoters. All genes could be regulated by different promoters or any combination of promoters.

The aromatic amino acid pathway genes could also be located solely on the chromosome or there could be any combination of chromosomally encoded aromatic amino acid pathway genes operating from plasmids.

The general recombinant DNA techniques used in the present invention, such as DNA isolation and purification, cleavage of DNA with restriction enzymes, construction of recombinant plasmids, introduction of DNA into microorganisms, and site directed mutagenesis, are described in many publications, including Manniatis et al., *Molecular Cloning—A Laboratory Manual*, Cold Springs Harbor Laboratory (1982) and *Current Protocols in Molecular Biology*, edited by Ausubel et al., Greene Publishing Associates and Wiley Interscience (1987).

II. Other Approaches to Isatin Removal

Ways to implement the adsorption or chemical conversion to a non-inhibitory compound in a fermentation are known to those skilled in the art. These may include, but are not limited to, the following.

Removal of Cell-Free Broth for Treatment

Cell-free broth can be removed from the fermentor by means of a separation device, such as a cross-flow filtration membrane or a centrifuge. The cell-free broth could then be treated by means shown in Examples 1 or 2. A heat exchange loop could be used to heat, and cool if necessary, the broth. Base for pH control could be added in the loop to increase alkalinity. In one embodiment of the present invention the isatin by-product is removed by treating the fermentation broth by elevating the pH to at least about 11 (by adding an appropriate base) and elevating the temperature to about 50–70° C. This treatment may occur over a period of time sufficient for the orange color of the broth to dissipate to a pale yellow (<12 hours, preferably about 2–5 hours or less). Alternatively, the broth could be passed over activated carbon or another adsorbent to remove the isatin [Freeman et al. (1993) "In situ product removal as a tool for bioprocessing," *Bio/technology* 11:1007–1012].

Addition of Adsorbent Directly to Bioconversion

Adsorbent could be added to the bioconversion to adsorb isatin. Activated carbon or another type of adsorbent could be added to the broth and then separated from the indigo after the fermentation.

Hydrolysis of Isatin by General Base Catalysis

The concentration of isatin could be lowered by the addition of elevated phosphate, which acts as a general base catalyst for the hydrolysis of isatin, to a fermentation. General base catalysis is shown in Example 4.

Experimental

EXAMPLE 1

Removing Isatin From a System Increases Indigo Production

Alleviation of Inhibition of Indigo Formation by Treatment with Heat and Elevated pH Two fermentations were performed with a strain capable of converting tryptophan to indigo [FM5(911-ISP, pCL-ISP#14)]. One was fed tryptophan and produced indigo while the control tank was not fed tryptophan and did not make any indigo. Broth was taken from each tank at 20 hours fermentation time and centrifuged to remove indigo and cells. Glucose was added to the supernatants to 10 g/L. For additional controls buffer samples containing 200 mM $K^{30}$ phosphate at pH 7.0 with 10 g/L glucose and ±5 mM isatin were prepared. To an aliquot of each broth and each buffer, 45% KOH was added to raise the pH to about 11.0. The solutions were placed on a hot plate and heated at about 50–70° C. until the orange color of the isatin solution changed to a pale yellow (about 2–5 hours). This color change, as determined in previous spectral experiments, indicates that isatin is hydrolyzed to isatic acid as shown in Scheme 1. At this time, all samples were cooled and the pH was readjusted to 7.0 with 85% phosphoric acid.

Scheme 1. Hydrolysis of Isatin

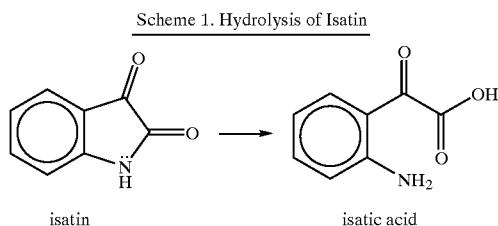

isatin                      isatic acid

Cells were taken at 21 hours from the fermentor in which no tryptophan was fed and centrifuged. After resuspension in 200 mM $K^+$ phosphate at pH 7.0 with 10 g/L glucose buffer at high cell density, equal aliquots of cells to give a final $A^{660}$ of 2 were placed into 25 mL of the pH and heat treated buffers and broth contained in a 250 mL baffled flasks, respectively (carried out in duplicate). The flasks were shaken for 30 minutes, at which time an initial indigo measurement was made (by dissolving 1 part culture in 10 parts or greater of DMF and measuring $A^{660}$) and indole was added to a concentration of 250 mg/L. Indigo production was measured spectrophotometrically at $A^{610}$ at the end of one hour and expressed as gram indigo per gram dry cell weight per hour. Results (for duplicate runs) are recorded in Table 1, comparing treated and untreated broth for the production of indigo.

TABLE 1

Indigo Production in pH and Heat Treated Fermentation Broth and Buffer as Determined by Shake Flask Assay

| | Heat and pH Treatment | | | |
|---|---|---|---|---|
| Medium | Treated | | Untreated | |
| Non-Trp Fed Broth | 0.400 | 0.446 | 0.442 | 0.442 |
| Trp Fed Broth | 0.314 | 0.347 | 0.0843 | 0.0797 |
| Buffer With Isatin | 0.327 | 0.327 | 0.0627 | 0.0764 |
| Buffer | 0.285 | 0.307 | 0.311 | 0.321 |

Results show that isatin or broth from an indigo producing bioconversion can reduce further indigo production. Treatment of broth or buffer to hydrolyze isatin to isatic acid relieves such inhibition.

EXAMPLE 2

Increase In Indigo Production By Treating Spent Broth From a Bioconversion With Activated Carbon Broth was collected from a bioconversion as in Example 1. Activated carbon was used to treat one aliquot of broth, with an aliquot of broth with no treatment serving as control. Indigo production rates, determined as in Example 1, are shown in Table 2. Results are shown as duplicates of the experiment.

TABLE 2

Indigo Production in Activated Charcoal Treated Fermentation Broth as Determined by Shake Flask Assay

| | Indigo Production | |
|---|---|---|
| Broth | (g/gDW/hr) | |
| Non-Carbon Treated | 0.057 | 0.048 |
| Carbon Treated | 0.115 | 0.122 |

These data show that treatment with carbon can relieve inhibition of indigo production. Release of inhibition was attributed to the removal of isatin by activated charcoal.

EXAMPLE 3

Isatin Is a Redox Cycler with Purified NDO

Recombinant NDO was purified, by published procedure [Haigler and Gibson (1990) "Purification and properties of $NADH$-ferredoxin$_{nap}$ reductase, a component of naphthalene dioxygenase from Pseudomonas sp. Strain NCIB 9816," *J. Bacteriol.* 172:457–464; Ensley and Gibson (1983) "Naphthalene dioxygenase: purification and properties of a terminal oxygenase component," *J. Bacteriol.* 155:505–511; Haigler and Gibson (1990) "Purification and properties of ferredoxin$_{nap}$, a component of naphthalene dioxygenase from Pseudomonas sp. Strain NCIB 9816," *J.*

Bacteriol. 172:465–468] from an E. coli strain overexpressing ferredoxin reductase (Rd), ferredoxin (Fd) and terminal oxygenase (ISP). The NDO operon had been placed under the phoA promoter. Purified components were stored at −80° C. until used. Isatin was established as an electron acceptor for ferredoxin reductase and ferredoxin by spectrally monitoring NADH oxidation at 340 nm in the presence of isatin. Assays were conducted as follows: 0.97 ml 50 mM Tris/HCl pH 7.5, 100 uM NADH, redox enzyme components and isatin. In some experiments NADH was also measured in the presence of the NDO substrate (R)-1,2,3,4-tetrahydro-1-naphthalene [(R)-THN]. In the absence of isatin or substrate no NADH oxidation was observed. Isatin did not change concentration in any assay as determined by monitoring its spectrum. Table 3 below summarizes results.

TABLE 3

Summary of Experiments Demonstrating Redox Cycling by Isatin

| [NADH], mM | Substrates (R)-THN = 1 mM Isatin = 250 uM | NADH Oxidized nmol/min/ml | Enzyme Components Present |
|---|---|---|---|
| 0.100 | (R)-THN | 9.0 | ISP, Fd, Rd |
| 0.100 | (R)-THN + isatin | 15.0 | ISP, Fd, Rd |
| 0.100 | isatin | 10.9 | ISP, Fd, Rd |
| 0.100 | isatin | 12.3 | Fd, Rd |
| 0.100 | isatin | 3.4 | Rd |
| 0.140 | isatin | 13.1 | ISP, Fd*, Rd |
| 0.100 | isatin | 12.5 | ISP, Fd*, Rd |

Note: [ISP] = 1 uM, [Rd] = 60 nM, [Fd] = 0.94 uM except when indicated by *, where [Fd] was 0.67 uM. Assay was not optimized for these experiments. In the absence of enzyme components no NADH oxidation was observed.

Results clearly show that isatin mediates the oxidation of NADH. Since isatin does not undergo any chemical change it acts as a redox cycler with the Rd and Fd components.

EXAMPLE 4

Demonstration of General Base Catalyzed Hydrolysis of Isatin

Hydrolysis of isatin by general base catalysis was demonstrated at several different concentrations of $KPO_4$ buffer pH 7 and 37° C. Hydrolysis was followed spectroscopically by monitoring disappearance of isatin and appearance of isatic acid at 302 and 368 nM, respectively. The starting concentration of isatin was 250 uM. The following table summarizes rates and demonstrates dependence of rate on buffer concentration. The table also shows the rate of isatin hydrolysis for a number of other anion and buffers, all at pH 7 and 37° C. Rates are expressed as half-life (τ½). Table 4 summarizes isatin hydrolysis rates in buffers.

TABLE 4

Summary of Data Demonstrating Hydrolysis of Isatin in Various Buffers

| Buffer | Concentration (mM) | τ½ |
|---|---|---|
| Tris-HCl | 50 | hours |
| Tris-AcOH | 50 | hours |
| Tris-HCl + NaCl | 50 100 | hours |
| Tris-HCl + KCl | 50 100 | hours |

TABLE 4-continued

Summary of Data Demonstrating Hydrolysis of Isatin in Various Buffers

| Buffer | Concentration (mM) | τ½ |
|---|---|---|
| K phosphate | 25 | 151 min |
|  | 50 | 85 min |
|  | 100 | 45 min |
|  | 200 | 22 min |
| Na phosphate | 100 | 35 min |
| K pyrophosphate | 100 | 35 min |
| Na triphosphate | 100 | 70 min |
| Na Carbonate | 100 | 80 min |

EXAMPLE 5

Isolation of Organism Producing Isatin Hydrolase

The isatin hydrolase-producing organism was isolated from a soil sample collected at a creosote plant in Terre Haute, Ind. Isolation was accomplished by an enrichment protocol using minimal salt medium [Stanier et al. (1957) J. Cell Comp. Phys. 49:25] containing 1 g of the soil sample and 1.7 mM indole as the sole carbon and energy source. After three serial passages of liquid enrichment cultures the organism was purified by plating liquid culture on 1.5% minimal salt medium agar plates with indole as the sole carbon source, followed by plating a growing colony on an LA plate and finally streaking a 1.5% minimal salt medium plate containing indole with cells derived from a single colony from the LA plate. Enrichment and purification were carried out at 30° C. Whole cells derived from a single colony and cultured in the original minimal salt medium with indole exhibited isatin hydrolase activity. This assay is described in Example 6. This colony was designated strain WW2.

EXAMPLE 6

Demonstration of Isatin Hydrolase Activity of Whole Cells of Organism (WW2) Isolated in Example 5

Cells grown in a minimal salt medium containing 1.7 mM indole were centrifuged. The cell pellet was resuspended in 50 mM Tris-HCl, pH 7.5 to an $OD^{600}$ of 2. To an aliquot of cell suspension, isatin was added to a concentration of 200 μM. The orange color disappeared in <30s. Cells were removed from the sample by centrifugation and the spectrum of the supernatant was recorded. This spectrum was identical to authentic isatic acid. HPLC analysis confirmed the identity of the product.

EXAMPLE 7

Demonstration of Isatin Hydrolase Activity in Cell Free Assay of WW2 and Apparent Native Molecular Size A 1:4 cell homogenate in 50 mM Tris-HCl, pH 7.5, of the organism isolated in Example 5 and grown either in LB medium containing 1.7 mM indole or in a minimal salt medium containing 1.7 mM indole was prepared by disrupting the cells in a French pressure cell. The homogenate was assayed directly or the supernatant and the pellet were assayed after 100,000 g centrifugation of the homogenates. Isatin hydrolase activity was found in the whole homogenates and in the high speed supernatants. Less than 5% of activity was detected in the high speed pellets. Equivalent activity was detected whether the cells were grown in rich or minimal medium. Cells grown in rich medium in the absence of indole had 20-fold reduced activity, indicating that indole induces the enzyme activity.

Apparent native molecular size was determined as follows. The crude homogenate from above was fractionated on DEAE cellulose with a 0 to 500 mM NaCl gradient in 50 mM Tris/HCl, pH 7.5. Enzymatic activity eluted at ~175 mM NaCl, however, 85% of the enzymatic activity was lost during this single step. Pooled and dialyzed fractions were further fractionated by a 30% to 40% $NH_4SO_4$ precipitation. Further losses in activity to about 10% of original activity resulted. Further treatment of the sample with TSK Q ion exchange chromatography yielded 1.4% of original activity on elution with a 0 to 500 mM NaCl gradient in the same buffer. This remaining activity was finally applied to a Sepharose S-100 gel filtration column. Enzymatic activity eluted corresponding to an apparent molecular weight of about 30 to 40,000 Da. Steps described above were monitored by spectrophotometric enzymatic assay. Either disappearance of isatin or appearance of isatic acid could be monitored at 302 or 368 nM, respectively, in 50 mM Tris/HCl, pH 7.5. Activity could also be detected on a 7.5% native acrylamide gel by overlaying the developed gel with a nitrocellulose membrane previously soaked in 5,7-dimethylisatin as described in Example 14. Enzyme was located by the appearance of a white spot on the peach colored membrane, the color having been imparted by incubation of the membrane with a 3.5 mg/10 ml 50 mM Tris HCl pH 7.5, 5,7-dimethylisatin solution for 20 min.

EXAMPLE 8

Increase in Indigo Production by Treating Spent Broth From a Bioconversion with Extract From WW2, Producing Isatin Hydrolase Broth was collected as in Example 1. A cytosolic cell extract from strain WW2, prepared by breaking cells with a French pressure cell and centrifugation at 100,000 g, was added to the broth and *E. coli* host cells and contacted for one hour prior to indole addition. Indigo production rate was measured and is shown in Table 5.

TABLE 5

Indigo Production in WW2 Cell Extract Treated Fermentation Broth as Determined by Shake Flask Assay

| Broth | Indigo Production (g/gDW/hr) |
|---|---|
| Non-Extract Treated | 0.071 |
| Extract Treated | 0.234 |

These data show that treatment with an enzyme capable of converting isatin to isatic acid relieves inhibition of indigo production.

EXAMPLE 9

Demonstration of Reduction of Isatin Concentration During a Bioconversion of Tryptophan to Indigo In the Presence of a Cytosolic Extract from *Pseudomonas putida* WW2

Cells of *Pseudomonas putida* strain WW2 were grown in a 10 L fermenter in a minimal salt medium with the addition of indole. Cell $OD^{600}$ of 4 was attained. Cells were harvested and an extract was prepared by breaking cells as a 1:1 suspension with the aid of a French press and centrifugation at 100,000 g. Beginning at 16 hours, this extract was added in 50 mL aliquots at 30 min. intervals for 4.5 hours to a bioconversion of tryptophan to indigo by FM5/911-ISP, pCL-ISP#14. Within one hour the isatin concentration had dropped from 0.4 mM to 0.06 mM. Over the same time interval the isatin concentration in a control tank rose to 0.95 mM, a level of isatin known to be inhibitory to NDO activity. The hydrolysis product isatic acid rose from 0.16 mM to 1.64 mM in the experimental tank, while in the control tank its concentration never exceeded 0.5 mM. This experiment showed that isatin hydrolase can significantly reduce the levels of isatin in broth during a fermentation. This experiment also suggests that isatin may be converted to some other product in the absence of isatin hydrolase since the sum of isatin plus isatic acid at the end of the fermentation is >7 mM while in the control tank this sum was <2 mM. This finding is consistent with the observation of elevated levels of indirubin in fermentations where isatin hydrolase is absent. Indirubin can form from the reaction of isatin with indoxyl, the precursor to indigo.

EXAMPLE 10

Taxonomic Classification of Organism Designated WW2

The organism isolated in Example 5 was typed by GC-FAME and Biolog®. These methods suggested the organism to be *Pseudomonas marginalis* or *Pseudomonas putida* type A1, respectively. Assays for phospholipase C activity [R. M. Berka, G. L. Gray and M. L. Vasil (1981) "Studies of phospholipase C (heat-labile homolysin in *Pseudomonas aeruginosa*)," *Infection and Immunity* 34:1071–1074] and the gelatin liquefaction activity [R. N. Krieg, ed., (1984) *Bergey's Manual of Systematic Bacteriology*, vol. 1 (J. G. Holt, series ed.), Williams and Wilkins, Baltimore, pp. 163–165] suggest the species to be *P. putida*. GC-FAME and Biolog® tests were done by Mirobe Inotech Laboratories, Inc. The new designation for WW2 is, therefore, *Pseudomonas putida* WW2.

EXAMPLE 11

Isolation of DNA Fragment Containing Isatin Hydrolase Activity

Total DNA was isolated from the organism described in Example 5 by the method of Harwood and Cutting [(1990) *Molecular Biological Methods for Bacillus*, John Wiley, New York, pp. 140–145]. All subsequent DNA manipulations were carried out by standard protocols found in Sambrook et al. [(1989) *Molecular Cloning—A Laboratory Manual*, 2nd ed., Cold Springs Harbor Laboratory] or as suggested by the manufacturers of kits. DNA was partially digested using 0.25 units of Sau3A restriction endonuclease (NEB) per 10 µg of DNA for one hour at 37° C. Digested DNA was fractionated on agarose gel and fragments of 1 to 10 kb were isolated by electroelution. A plasmid library was constructed using the pTrc99A expression vector (Pharmacia, catalog #27-5007). The ligation mixture was transformed into competent Sure Cells® (Stratagene, catalog #200238) which were subsequently plated onto 40, 15 cm 2YT plates containing 50 µg of carbenicillin, and 50 µg of indole per ml, and 1 mM IPTG. After overnight growth at 37° C., colonies were lysed by lightly spraying with a solution containing 10 mg/mL of lysozyme and 25 mM EDTA and incubating at room temperature for 20 min. The partially lysed cells were then overlaid with a nitrocellulose filter that had been impregnated for 20 to 30 min. in 50 mM Tris-HCl, pH 7.5, and 2 mM 5,7-dimethylisatin (5,7-dimethylisatin was added from a 20 mM stock solution made up in ethanol). Positive clones were identified as a decolorized dot in a peach colored background. A total of 3 positive clones out of 3,000 were identified. Picked colonies were purified by two rounds of colony purification on solid LB plates. After isatin hydrolase activity was demonstrated as described in Example 12 below, restriction analysis of the cloned DNA showed it to be about 6.8 kb in size. Subcloning yielded a 2.3 kb and subsequently a 1 kb fragment exhibiting isatin hydrolase activity when assayed in whole cell assay described in Example 12. The complete nucleotide sequence of the 1 kb fragment was subsequently determined and is shown in FIG. 3 (Seq ID No. 1). The amino acid sequence was deduced as shown in Seq ID No. 2 .

EXAMPLE 12

Demonstration of Isatin Hydrolase Activity in *E. coli* Cloning Organism

Whole cells of positive clones identified in Example 11 were assayed for isatin hydrolase activity similarly as in Example 6, except that the medium was LB containing carbenicillin. IPTG was not required for induction of cells containing the full length fragment or the 2.3 kb fragments, suggesting that these isolated DNA fragments contained an endogenous promoter. The subcloned 1 kb fragment, however, required IPTG to express maximal activity.

EXAMPLE 13

Construction of Plasmid pCL-IST1

As is shown in FIG. 7, construction of this plasmid was accomplished by digestion of plasmid pAK1 with SalI, isolation of the 3.2 kb fragment containing the tnaA structural gene, by agarose gel electrophoresis, and ligation of this fragment into plasmid pCL-IH-S1 after its linearization with SalI.

EXAMPLE 14

Construction of Plasmid pCL-IHA

As is shown in FIG. 8, this plasmid was constructed in two steps from plasmids pTrc-IH#2, pMB2190 and pCL1920. Digestion of plasmids pMB2190 [Darzins et al. (1986) *Gene* 42:293–302] and pTrc-IH#2 with EcoRI, followed by ligation and transformation, allowed the isolation of a colony resistant to ampicillin and kanamycin which bore the plasmid pTrc-IH#2-kan. This cloning step allowed for the isolation of a 2.5 kb SalI fragment from pTrc-IH#2-kan containing the isatin hydrolase gene. This fragment was then cloned into the unique SalI site of pCL1920 vector to yield pCL-IHA as one of the products.

EXAMPLE 15

Absence of Inhibition of Indigo Production by Fermentation Broth From a Strain Containing the 2.3 kb Fragment Harboring the Isatin Hydrolase Gene Transformation of Production Hosts Transformation of *E. coli* strains was carried out by the use of the $CaCl_2$ method for rendering cells competent as described in Manniatis et al., *Molecular Cloning—A Laboratory Manual*, Cold Springs Harbor Laboratory, p. 250 (1982).

Bioconversions making indigo were performed with FM5 (911-ISP) and FM5 (911-ISP,pCL-IHA) (FIG. 8). The first strain was the control strain not containing the gene for isatin hydrolase, while the second strain contained a 2.3 kb DNA fragment harboring the isatin hydrolase gene. Broth and cells were collected from each fermentation and broth was supplemented with glucose as in Example 1. The cells were then resuspended either in the glucose supplemented broths, or buffer for indigo shake flask assays as in Example 1. Result are shown in Table 6.

TABLE 6

Effect of Isatin Hydrolase Gene on Indigo Production in Shake Flask Assays

| Medium | Strain | Indigo Production (g/gDW/hr) |
|---|---|---|
| Broth | FM5(911-ISP) | 0.0416 |
| Buffer | FM5(911-ISP) | 0.115 |
| Broth | FM5(911-ISP,pCL-IHA) | 0.286 |
| Buffer | FM5(911-ISP,pCL-IHA) | 0.264 |

Data comparing buffer and broth show that broth from a strain harboring isatin hydrolase is not inhibitory to indigo production, while that from a broth without isatin hydrolase is inhibitory.

EXAMPLE 16

DNA Sequence of the Isatin Hydrolase Gene

DNA sequence of the 1 kb fragment isolated in Example 11 was determined by a modification of the dideoxy chain termination method [Sanger et al. (1977) *Proc. Natl. Acad. Sci. USA* 74:5463–5467]. An open reading frame (ORF) consisting of 780 bp was identified. There were 144 bp of 5'-untranslated and 82 bp of 3'-untranslated DNA, respectively, giving a total of 1006 bp for the cloned DNA. The sequence data is shown in FIG. 3 (Seq ID No.1).

EXAMPLE 17

Purification of Isatin Hydrolase

Partial purification of the enzyme coded for by the 1 kb DNA fragment has been achieved. This was accomplished by modifying the 1 kb fragment by joining 6 histidine codons in frame to the 5' end of the ORF described in Example 14 and growing cells transformed with this construct under IPTG induced conditions. Cells suspended in 50 mM Tris-HCl, pH 7.5, at one part cell pellet and one part buffer and ruptured in a French pressure cell. The homogenate was further diluted with an equal volume of the same buffer and centrifuged at 100,000 g. The high speed supernatant was passed over a Ni-NTA resin column according to the manufacturer's recommendations (QIAGEN, Inc., CA). Enzymatic activity bound to the column and purification was achieved by washing the column with 50 mM Na phosphate, 300 mM NaCl, 10% glycerol at pH 6.0 (wash buffer) until the $A_{280}$ dropped below 0.04 absorbance units. The column was then eluted with a gradient of 0–0.5 M imidazole in 50 mL of wash buffer. Fractions containing enzymatic activity, as detected by isatin hydrolysis, were electrophoresed on SDS-PAGE [U. K. Laemmli (1970) *Nature* 277:680–685]. The silver stained gel showed a major band at 33,000 Da and only traces of other components in the most pure fraction. These results are in agreement with the molecular weight determination of the protein from the native oraganize described in Example 7. In this case, gel permeation chromatography gave an estimate of 30 to 40 kDa for the protein exhibiting isatin hydrolase activity. These combined results indicate that isatin hydrolase is a monomer in its native state.

EXAMPLE 18

Demonstration of Diminution of Indirubin Levels Due to Isatin Hydrolase In Indigo Fermentations Fermentations in 14 L fermenters were carried out as usual, either with an indigo-producing strain containing the gene for isatin hydrolase or with this gene absent. Samples were taken as a function of fermentation time and analyzed as follows: 1 ml fermentation broth was centrifuged for 15 min. at 12,000 g, supernatant was removed and the pellet resuspended in THF/DMSO (1/1; 1 ml) and vortex for 1 min. The mixture was recentrifuged at 12,000 g. The supernatant was used for HPLC analysis as described in Example 20.

TABLE 7

Results for Indirubin Analyses as a Function of Presence and Absence of Isatin Hydrolase and Fermentation Time

| time [h] | Run X-BLU-22720 +hydrolase [g indirubin/l] | Run X-BLU-22724 −hydrolase [g indirubin/l] |
|---|---|---|
| 4  | 0     | 0     |
| 8  | 0     | 0     |
| 12 | 0     | 0     |
| 16 | 0.0   | 0.0   |
| 20 | 0.032 | 0.044 |
| 28 | 0.011 | 0.072 |
| 32 | 0.052 | 0.11  |
| 36 | 0.059 | 0.155 |
| 40 | 0.033 | 0.154 |
| 44 | 0.064 | 0.250 |
| 48 | 0.094 | 0.192 |

Additional endpoint analyses (at about 48 h, the usual termination of fermentations) were carried out on a number of fermenters by the same method. Results for these are reported in the table below.

TABLE 8

(Indirubin HPLC Data for Runs 22741, 22743–46 (with IH) and 22598 (without IH)

| Fermenter Run ID# | Isatin Hydrolase | Indirubin [g/l prep.] |
|---|---|---|
| 22741 | + | 0.27 |
| 22743 | + | 0.09 |
| 22744 | + | 0.10 |
| 22745 | + | 0.06 |
| 22746 | + | 0.17 |
| 22717 | + | 0.09 |
| 22756 | + | 0.09 |
| 22757 | + | 0.13 |
| 22759 | + | 0.14 |
| 22760 | + | 0.13 |
| 22761 | + | 0.27 |
| 22598 | − | 1.13 |
| cone 1 | − | 0.91 |

Conclusion: These experiments show that there is a two-fold or greater reduction in level of indirubin due to the presence of adding the isatin hydrolase gene to the indigo producing strain.

EXAMPLE 19

Demonstration of Diminution of Indirubin Levels Due to isatin Hydrolase in Denim Dyed with Indigo from E. coli Fermentation Process Indirubin level of indigo dyed denim correlate with a red cast of the dyed cloth and resistance to bleaching of indigo dyed denim to achieve a 'bleached out' fashion look. Experiments below demonstrate higher levels of indirubin in denim dyed with indigo from the E. coli fermentation process without isatin hydrolase than with isatin hydrolase. Indirubin levels in denim samples were determined as follows: 2 grams of denim were extracted with 150 ml ethanol in a soxlet apparatus for 1.5 hours. Extracts were dried down in a rotary evaporator and brought up in 1 ml THF:DMSO solvent for HPLC analysis according to Example 20.

TABLE 9

Indirubin Content of Denim Dyed with Indigo Produced by Host Cells with and Without Isatin Hydrolase

| Denim Sample ID | Sample Description | Isatin Hydrolase | Indirubin Level in Indigo Dye | Indirubin Concentration (mg/g denim) |
|---|---|---|---|---|
| NI94241 | fermentation indigo | − | 0.91 mg/mL 20% paste | 0.061 |
| NI11095 | fermentation indigo | + | 0.46 mg/mL 20% paste | 0.011 |
| BC034 | chemical indigo | N/A | 0.03 mg/mL 20% paste | below detection limit | le;2qThe results show that indirubin levels are lower on denim dyed with indigo containing lower levels of indirubin. The correlation is not linear and the factors controlling the relationship are not fully understood. Additional qualitative observations (by experts in the dyeing industry) are in agreement with quantitative observations.

EXAMPLE 20

Demonstration of Effect of Indirubin on Bleach Down of Denim Dyed with Indigo Typical Procedure for Dyeing of Denim with Indigo
1. Cloth Hydration (predyeing conditioning)
   A. Cut 9" by 15" sections (swatches) of bull denim (two per dyebath)
   B. Soak in hot tap water overnight (minimum of 1 hr)
2. Dyebath Preparation
   A. Make stock mix using 60 g 20% paste. While stirring on hot plate add:
   74.9 g Dl H2O
   23.0 g 50% NaOH
   60.0 g 20% indigo paste (with 5% NaOH)
   Heat to ~70° C.
   Add 8.16 g sodium dithionite
   Stir to dissolve then remove from heat.
   B. Make balance solution (use container in which dyeing will be performed):
   4,383 g deionized water
   25.3 g 50% NaOH
   15.4 g sodium dithionite
   Add 138.4 g of stock mix.
   Stir to mix and then stop mixing.
3. Dyeing Procedure
   A. Water soaked swatches are pressed between laundry-type wringer to remove excess water and assure uniform water content of all swatches prior to dyeing.
   B. Swatches are dipped according to following protocol. Submerge swatch in dyebath for 20 seconds, remove excess dye bath liquor by passing cloth through wringer, expose cloth to ambient air (skying) for approximately 3 minutes for oxidation of leucoindigo to indigo between dips.

(Table of dipping schedule indicating beginning and end of dips 1 through 5 in minutes and seconds; wringing and skying is carried out between dips.)
Dip 1 0:30–0:50
Dip 2 4:00–4:20
Dip 3 7:30–7:50
Dip 4 11:00–11:20
Dip 5 14:30–14:50
Following last dip, pass through wringer and sky for 5 minutes.
C. Rinse by dipping in cold water followed by dipping in hot water. Pass cloth through wringer and dry.
D. When required, cut each swatch into fifteen (15) 3" by 3" squares.

Bleaching Indigo-Dyed Swatches with Sodium Hypochloride (Simulating Bleaching Conditions Used to Create Fashion Look)

Bleaching Procedure

A. Bleach bath Preparation
2.6 g sodium hypochloride to 1 L deionized water (hypochloride is added from a 5.25% stock solution)
Heat to 50° C.

B. Capacity of Bath
No more than 1:50 ratio of cloth to bleach solution (200 g dry cloth per 10 L bleach solution)
(Bleaching is carried out as specified in appropriate Examples)

C. Addition Times
Separate the 15 small swatches into five groups of three. Prewet in Dl water for minimum of five minutes. Four of these groups will be added to the bleach solution. Time of addition will be 0, 10, 20 and 25 minutes for time in bleach of 30, 20, 10 and 5 minutes.

D. Quenching and Washing
Remove swatches and place in cold water
Quickly rinse and add to ~2 L of 10 g/L sodium bisulfite
Rinse in water and add ~2 L of 10 g/L Tide w/o bleach
Rinse thoroughly
Dry swatches thoroughly E. Read L-values on Hunter Lab color meter Indirubin was added at 10 mg and 70 mg indirubin/g of indigo to commercial chemical indigo paste. The 'doped' dye was mixed well and denim cloth was dyed according to the dyeing and bleaching protocols described in this Example 20. Color values were read as provided below. The plotted data is shown in FIG. 9.

Evaluation of Efficiency of Bleaching of Indigo Dyed-Denim with Sodium Hypochloride Effect of bleaching was measured as L-value with a Hunter Lab color meter (Hunter Associates Laboratory, Inc., Reston, Va.). L-value designates the 'lightness' of a sample, with 0 representing black and 100 representing pure white. Results are expressed in delta L-value.

Determination of Indirubin Concentration by HPLC

The method is as follows: column, 250×4.6 mm, RP-18, 5 $\mu$m; detection at 254 nm; solvent system used, solvent A—90% water, 10% acetonitrile, 2 g/L tetrabutylammoniumbromide, solvent B—90% acetonitrile, 10% water, 2 g/L tetrabutylammoniumbromide.

| Gradient program: | | | |
|---|---|---|---|
| % A | % B | time | flow (ml/min) |
| 65 | 35 | 0 | 0.7 |
| 65 | 35 | 2 | 0.7 |
| 35 | 65 | 50 | 0.7 |
| 65 | 35 | 51 | 0.7 |
| 65 | 35 | 55 | 0.1 |

Retention time of indirubin in this system is 31.8 min., and indigo elutes at 27.5 min.

The data in FIG. 9 shows that at elevated levels of indirubin, bleaching is inhibited. Although the difference seems small at 30 min., the skilled artisan viewing cloth dyed with indigo, with or without indirubin, recognizes the difference as being significant. While the sample without indirubin and with 10 mg indirubin added met specifications, the sample with 70 mg indirubin did not.

What is claimed is:

1. An isolated DNA fragment coding an enzyme having isatin-removing activity comprising the nucleotide sequence of SEQ ID No. 1.

2. An expression vector comprising said DNA fragment of claim 1.

3. A host cell transformed with said expression vector of claim 2.

4. An expression vector comprising said DNA fragment of claim 1.

5. A host cell transformed with said expression vector of claim 4.

6. An improved process for the production of indigo in a suitable host microorganism, the process comprising cultivating the microorganism under conditions facilitating the accumulation of indoxyl, the improvement comprising introducing into the host microorganism a DNA fragment coding isatin-removing enzyme activity wherein said DNA fragment coding isatin-removing enzyme activity is a DNA fragment as shown in SEQ ID No. 1.

7. The process of claim 6 wherein said DNA fragment encoding isatin-removing enzyme activity is integrated into the chromosome of the microorganism.

8. The process of claim 6 wherein said DNA fragment encoding isatin-removing enzyme activity is contained in one or more extrachromosomal element(s) capable of directing expression of said DNA fragment under appropriate conditions.

9. The process of claim 6 wherein the suitable host microorganism comprises endogenous or exogenous DNA required for the production of indigo from glucose.

10. The process of claim 9 wherein said endogenous or exogenous DNA is selected from the group consisting of a DNA coding one or more enzyme(s) of a tryptophan operon, a DNA fragment coding an oxygenase enzyme capable of converting indole to indoxyl, and a DNA fragment coding an enzyme capable of converting tryptophan to indole.

11. The process of claim 10 wherein the DNA fragment(s) coding one or more of the enzymes of a tryptophan operon, an oxygenase enzyme or an enzyme capable of converting tryptophan to indole are integrated into the chromsome of the microorganism.

12. The process of claim 10 wherein the DNA fragment(s) coding one or more of the enzymes of a tryptophan operon, an oxygenase enzyme or an enzyme capable of converting tryptophan to indole are contained in one or more extrachromosomal element(s) capable of directing expression of said DNA fragments under appropriate conditions.

13. The process of claim 10 wherein said DNA fragment coding for an oxygenase enzyme codes for an aromatic dioxygensae or an aromatic monooxygenase.

14. The process of claim 10 wherein said DNA coding the tryptophan operon comprises a tryptophan synthase mutation capable of yielding accumulation of indole.

15. The process of claim 14 wherein said tryptophan synthase mutation is trpB382.

16. The process of claim 6 wherein the suitable host microorganism comprises endogenous or exogenous DNA required for the production of indigo from tryptophan.

17. The process of claim 16 wherein said endogenous or exogenous DNA codes an enzyme capable of converting tryptophan to indole.

18. The process of claim 17 wherein said DNA codes a tryptophanase enzyme.

19. The process of claim 16 wherein said endogenous or exogenous DNA is integrated into the chromosome of the host microorganism.

20. The process of claim 16 wherein said endogenous or exogenous DNA is contained in one or more extrachromosomal element(s) capable of directing the expression of said DNA under appropriate conditions.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 1006 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
CGAGGACTGG AGAACAGAGA GCTATAAGAT TTATGCAATT TACCCGTCAA GAAAAAACAT      60

GAACCCAGCA CTTCGGGTTT TTCTGGACTA TATGTACCTT CACCTCCCGC ATCAGATTTC     120

CGGGACTTCT TTCGAGGAAA ACTCATGACC AGCATTAAAC TCCTTGCAGA GAGTCTGCTC     180
```

-continued

| | |
|---|---|
| AAAGACAAAA TAAAGATCGT CGATCTATCG CACACCTTGA GATCCGAATT TCCGACACTG | 240 |
| ACATTACCTC CTCAGTTTGG GCAAACCTGG GCGTTCAAGA AGGAGGAAAT ATCGCGCTAC | 300 |
| GACGACCGTG GGCCCGCTTG GTACTGGAAC AACTTTTCCT GCGGCGAACA CACTGGTACT | 360 |
| CACTTTGATG CCCCAGTCCA TTGGGTCACA GGCGAATCCG TGCCTGAGAA CTCAGTAGAT | 420 |
| CGTATTGACC CACAGCGCTT TATGGCACCG GCAGTAGTGA TTGATGCCTC TAAAGAGGTA | 480 |
| CTAGAAAATC CGGACTGGGT TCTAGAGCCA GAATTTATCC AGGAGTGGGA GAAACTGCAT | 540 |
| GGCCGGATCG AAGCCGGTTC CTGGTTTCTA CTCCGGACAG ATTGGTCGAA GAAAATCAAT | 600 |
| AACCCGCTTG AGTTTGCTAA CCTGATAGAC GGCGCACCTC ACACGCCAGG CCCAAGCCAG | 660 |
| CGTACAGTTG AATGGCTTAT CGCCGAACGT GATGTCGTGG GCTTTGGGGT TGAGACGATC | 720 |
| AATATTGATG CGGGCCTTTC AGGCCGCTGG GAAGTTCCAT ACCCTTGCCA CAACAAGATG | 780 |
| CTGGGAGCAG GACGATTCGG GCTGCAGTGC TTGAACAATC TTGACCTGTT ACCACCAACA | 840 |
| GGAGCAGTAA TCATCTCCGC TCCACTGAAG ATCGAAGATG GCTCAGGCAG CCCGCTGCGG | 900 |
| GTACTGGCTA TTTTTGATCG AGAATAACTG AGAGTACCCT GGGGCCGATA GACTCATCGG | 960 |
| CCCCAAGTGA GTGTTCTCTA CTCGTAGTAG AAGCGAAGAC CAACTT | 1006 |

(2) INFORMATION FOR SEQ ID NO: 2:

(i) SEQUENCE CHARACTERISTICS:
        (A) LENGTH: 260 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Thr Ser Ile Lys Leu Leu Ala Glu Ser Leu Leu Lys Asp Lys Ile
 1               5                  10                  15

Lys Ile Val Asp Leu Ser His Thr Leu Arg Ser Glu Phe Pro Thr Leu
                20                  25                  30

Thr Leu Pro Pro Gln Phe Gly Gln Thr Trp Ala Phe Lys Lys Glu Glu
            35                  40                  45

Ile Ser Arg Tyr Asp Asp Arg Gly Pro Ala Trp Tyr Trp Asn Asn Phe
50                  55                  60

Ser Cys Gly Glu His Thr Gly Thr His Phe Asp Ala Pro Val His Trp
65                  70                  75                  80

Val Thr Gly Glu Ser Val Pro Glu Asn Ser Val Asp Arg Ile Asp Pro
                85                  90                  95

Gln Arg Phe Met Ala Pro Ala Val Val Ile Asp Ala Ser Lys Glu Val
            100                 105                 110

Leu Glu Asn Pro Asp Trp Val Leu Glu Pro Glu Phe Ile Gln Glu Trp
        115                 120                 125

Glu Lys Leu His Gly Arg Ile Glu Ala Gly Ser Trp Phe Leu Leu Arg
    130                 135                 140

Thr Asp Trp Ser Lys Lys Ile Asn Asn Pro Leu Glu Phe Ala Asn Leu
145                 150                 155                 160

Ile Asp Gly Ala Pro His Thr Pro Gly Pro Ser Gln Arg Thr Val Glu
                165                 170                 175

Trp Leu Ile Ala Glu Arg Asp Val Val Gly Phe Gly Val Glu Thr Ile
            180                 185                 190

Asn Ile Asp Ala Gly Leu Ser Gly Arg Trp Glu Val Pro Tyr Pro Cys
        195                 200                 205
```

```
His Asn Lys Met Leu Gly Ala Gly Arg Phe Gly Leu Gln Cys Leu Asn
    210                 215                 220

Asn Leu Asp Leu Leu Pro Pro Thr Gly Ala Val Ile Ile Ser Ala Pro
225                 230                 235                 240

Leu Lys Ile Glu Asp Gly Ser Gly Ser Pro Leu Arg Val Leu Ala Ile
                245                 250                 255

Phe Asp Arg Glu
            260

(2) INFORMATION FOR SEQ ID NO: 3:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO: 3:

Met Thr Ser Ile Lys Leu Leu Ala Glu Ser Leu Leu Lys
1               5                   10
```